US008455094B2

(12) United States Patent
Omata et al.

(10) Patent No.: US 8,455,094 B2
(45) Date of Patent: *Jun. 4, 2013

(54) MEDICAL DEVICE HAVING SURFACE LUBRICITY IN WET STATE

(75) Inventors: Kazuya Omata, Shizuoka (JP); Maeda Naoyuki, Shizuoka (JP); Onishi Makoto, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/185,979

(22) Filed: Jul. 19, 2011

(65) Prior Publication Data

US 2011/0274917 A1 Nov. 10, 2011

Related U.S. Application Data

(63) Continuation of application No. PCT/JP2010/050804, filed on Jan. 22, 2010.

(30) Foreign Application Priority Data

Jan. 28, 2009 (JP) ................................. 2009-017097

(51) Int. Cl.
*B32B 27/06* (2006.01)
*B32B 27/16* (2006.01)
*B32B 9/00* (2006.01)
*B32B 33/00* (2006.01)
*H05H 1/00* (2006.01)

(52) U.S. Cl.
USPC ........ 428/333; 428/336; 428/411.1; 428/420; 427/535

(58) Field of Classification Search
None
See application file for complete search history.

(56) References Cited

U.S. PATENT DOCUMENTS

| 4,385,635 A | * | 5/1983 | Ruiz ............................. 600/435 |
| 5,441,488 A | | 8/1995 | Shimura et al. |
| 5,670,558 A | | 9/1997 | Onishi et al. |

(Continued)

FOREIGN PATENT DOCUMENTS

| JP | 5-309131 A | 11/1993 |
| JP | 6-285152 A | 10/1994 |

(Continued)

OTHER PUBLICATIONS

International Search Report (PCT/ISA/210) issued on Apr. 6, 2010, by Japanese Patent Office as the International Searching Authority for International Application No. PCT/JP2010/050804.

(Continued)

*Primary Examiner* — Ramsey Zacharia
(74) *Attorney, Agent, or Firm* — Buchanan Ingersoll & Rooney PC

(57) ABSTRACT

A medical device wherein a surface lubricating layer and one of various polymer bases are fixed with each other firmly by a relatively simple technique. The medical device permanently exhibits excellent surface lubricity when in use. The medical device has a lubricating surface when wet, and includes a base layer at least the surface of which is composed of a polymer material, a compound (thiol compound) which is supported on at least a part of the base layer and has a plurality of thiol groups in each molecule, and a surface lubricating layer which covers the thiol compound and is composed of a hydrophilic polymer that has a reactive functional group.

15 Claims, 16 Drawing Sheets

U.S. PATENT DOCUMENTS

| | | | |
|---|---|---|---|
| 5,731,387 A | * | 3/1998 | Zajaczkowski ............ 525/330.2 |
| 6,828,028 B1 | | 12/2004 | Fukui et al. |
| 2003/0134100 A1 | | 7/2003 | Mao et al. |

FOREIGN PATENT DOCUMENTS

| | | |
|---|---|---|
| JP | 8-019599 A | 1/1996 |
| JP | 8-033704 A | 2/1996 |
| JP | 2000-039737 A | 2/2000 |
| JP | 2005-510608 A | 4/2005 |
| JP | 2007-267757 A | 10/2007 |
| JP | 2007-289299 A | 11/2007 |

OTHER PUBLICATIONS

U.S. Appl. No. 13/186,117, filed Jul. 19, 2011, "Medical Device Having Surface Lubricity in Wet State", naming Kazuya Omata, Naoyuki Maeda, and Makoto Onishi as inventors.

International Search Report (PCT/ISA/210) issued on Mar. 16, 2010, by Japanese Patent Office as the International Searching Authority for International Application No. PCT/JP2010/051056.

* cited by examiner

MEDICAL DEVICE HAVING SURFACE LUBRICITY IN WET STATE

This application is a continuation of International Application No. PCT/JP2010/050804 filed on Jan. 22, 2010, and claims priority to Japanese Application No. 2009-017097 filed on Jan. 28, 2009, the entire content of both of which is incorporated herein by reference.

TECHNICAL FIELD

The present invention generally relates to a medical device whose surface has lubricity in wet state.

BACKGROUND DISCUSSION

Medical devices to be inserted into a living body, such as catheters, guide wires, indwelling needles and the like, can exhibit good lubricity in order that damage to tissue such as blood vessels is reduced and handleability of an operator is improved. Hence, there have been developed and put into practice methods of coating a base material surface with a hydrophilic polymer having lubricity. In such medical devices, elution and peeling-off of the hydrophilic polymer from the base material surface presents a problem in maintaining safety and handleability.

In order to avoid such a problem, Japanese Patent Laid-Open No. Hei 8-33704 discloses a medical device wherein a water-soluble or water-swelling polymer is dissolved in a solvent capable of swelling a base material of the medical device to prepare a polymer solution, and the base material of the medical device is swollen by immersion in the polymer solution, followed by crosslinking or converting the polymer into a higher molecular weight product on the base material surface thereby forming a surface lubricating layer on the base material surface.

In the method described in the above-indicated Japanese Patent Laid-Open No. Hei 8-33704, the surface lubricating layer can be strongly fixed on the base material to some extent. Especially, where the base material per se is swollen with a hydrophilic polymer solution, very strong fixing is enabled by the formation of an interpenetrating network structure of the base material polymer and the hydrophilic polymer formed as the surface lubricating layer. On the other hand, where the base polymer is unlikely to be swollen with a hydrophilic polymer solution, the hydrophilic polymer serving as the surface lubricating layer is fixed to the base material only by the insolubilizing effect, involving a higher risk that the surface lubricating layer is peeled off when compared with the polymer base material forming the interpenetrating network structure. Thus, there is a need for a coating method wherein a hydrophilic polymer can be fixed more strongly on a sparingly swelling polymer base surface.

For a method of strongly fixing a hydrophilic polymer on a polymer base surface in large amounts, Japanese Patent Laid-Open No. 2007-289299 discloses a medical device, which includes a polymer material serving as a base layer and having a first higher-order structure in the molecule and a first functional group provided at least at one terminal of the first higher-order structure, and a hydrophilic polymer having, in the molecule, a second higher-order structure capable of interacting with the first higher-order structure and a second functional group capable of hydrogen bonding with the first functional group and provided at least at one terminal of the second higher-order structure.

However, the method set out in the above-mentioned Japanese Patent Laid-Open No. 2007-289299 has a problem in that limitation is placed on the combination of a base polymer and a hydrophilic polymer.

SUMMARY

The medical device disclosed here can permanently show excellent surface lubricity in use by strongly fixing a variety of polymer base materials and surface lubricating layers by a relatively simple procedure.

A medical device having surface lubricity in wet state is disclosed and includes:

a base layer at least a surface of which is made of a polymer material;

a compound supported on at least a part of said base layer and having a plurality of thiol groups (—SH: which may be called a mercapto group, a sulfhydryl group or a hydrosulfide group) (which may be sometimes referred to simply as "thiol compound" hereinafter) in the molecule; and a surface lubricating layer that covers said compound having a plurality of thiol groups in the molecule and is made of a hydrophilic polymer having a reactive functional group, wherein said compound having the thiol groups is supported (fixed) on the base layer by irradiation of an ionized gas plasma, and said compound having the thiol groups and said hydrophilic polymer having the reactive functional group are reacted to cause the surface lubricating layer to be bound to the base layer.

According to one aspect of the disclosed example, the medical device has surface lubricity in wet state, wherein the device is obtained by coating a solution dissolving said compound having the thiol groups (thiol compound solution) onto a surface of said base layer, and subsequently irradiating an ionized gas plasma (plasma treatment after the coating of the thiol compound) whereby said compound having the thiol groups is supported (fixed) on the base layer.

According to one aspect of the disclosed example, the medical device has surface lubricity in wet state, wherein the device is obtained by irradiating an ionized gas plasma on a surface of said base layer, coating a solution dissolving said compound having the thiol groups onto a surface of said base layer, and irradiating an ionized gas plasma again whereby said compound having the thiol groups is supported (fixed) on the base layer.

According to another aspect of the disclosed example, the medical device is obtained by, after coating of the solution dissolving said compound having the thiol groups onto the surface of the base layer, irradiating the ionized gas plasma, and subjecting to a heat treatment whereby said compound having the thiol groups is supported (fixed) on the base layer.

According to another aspect of the disclosed example, the medical device is obtained by irradiating an ionized gas plasma (plasma treatment prior to coating of the thiol compound) on the surface of said base layer prior to coating of the solution dissolving said compound having the thiol groups onto the surface of said base layer whereby said compound having the thiol groups is supported (fixed) on the base layer.

According to another aspect of the disclosed example, the medical device is obtained by, after coating of the solution dissolving said compound having the thiol groups onto the surface of the base layer, subjecting to heat treatment whereby said compound having the thiol groups is supported (fixed) on the base layer.

A method of making a medical device having surface lubricity in a wet state involves:

coating a compound, having a plurality of thiol groups in the molecule, on a medical device comprising a base layer, with at least a surface of the base layer made of a polymer material, wherein the compound is coated on the polymer material;

providing a surface lubricating layer made of a hydrophilic polymer having a reactive functional group, on the coating formed from the compound having a plurality of thiol groups;

reacting the compound having the thiol groups with the hydrophilic polymer having the reactive functional group to cause the surface lubricating layer to be bound to the base layer, wherein the surface of the base layer or the coating formed from the compound having a plurality of thiol groups is irradiated with an ionized gas plasma.

BRIEF DESCRIPTION OF THE DRAWING FIGURES

DETAILED DESCRIPTION

One aspect of the disclosure here described by way of example is a medical device having surface lubricity in wet state is disclosed, including a base layer, at least a surface of which is made of a polymer material (which may be hereinafter referred to simply as "polymer base layer," a compound supported on at least a part of the base layer and having a plurality of thiol groups (—SH: which may be called a mercapto group, a sulfhydryl group or a hydrosulfide group) (which may be sometimes referred to simply as "thiol compound" hereinafter) in the molecule, and a surface lubricating layer covering the compound having a plurality of thiol groups in the molecule and made of a hydrophilic polymer having a reactive functional group, wherein the compound having the thiol groups is supported (fixed) on the base layer by irradiation of an ionized gas plasma (which may be hereinafter referred simply as "plasma treatment"), and the compound having the thiol groups and the hydrophilic polymer having the reactive functional group are reacted to cause the surface lubricating layer to be bound to the base layer. Accordingly, the base layer surface and the surface lubricating layer can be strongly fixed to each other through the thiol compound by the irradiation of the ionized gas plasma.

Further, after the support (fixing) of the thiol compound on the base layer surface, when the reactive functional group (e.g. an epoxy group, an isocyanate group or the like) of the hydrophilic polymer and the residual thiol groups of the thiol compound are reacted to form the surface lubricating layer, the surface lubricating layer can be strongly fixed through the thiol compound on the base layer surface made of a variety of polymer materials by a simple procedure. Thus, surface lubricity that is excellent in use can be permanently shown.

Exemplary embodiments are described with reference to the accompanying drawings.

Figure 1A:
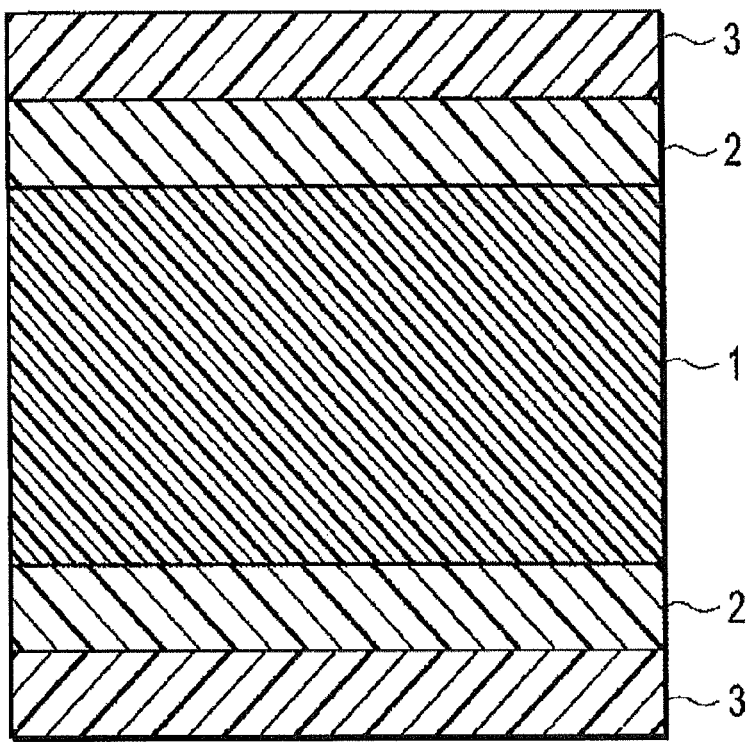
FIG. 1A is a partial sectional view schematically showing a laminate structure of a surface according to an exemplary embodiment of a medical device having surface lubricity in a wet state.
Figure 1B:
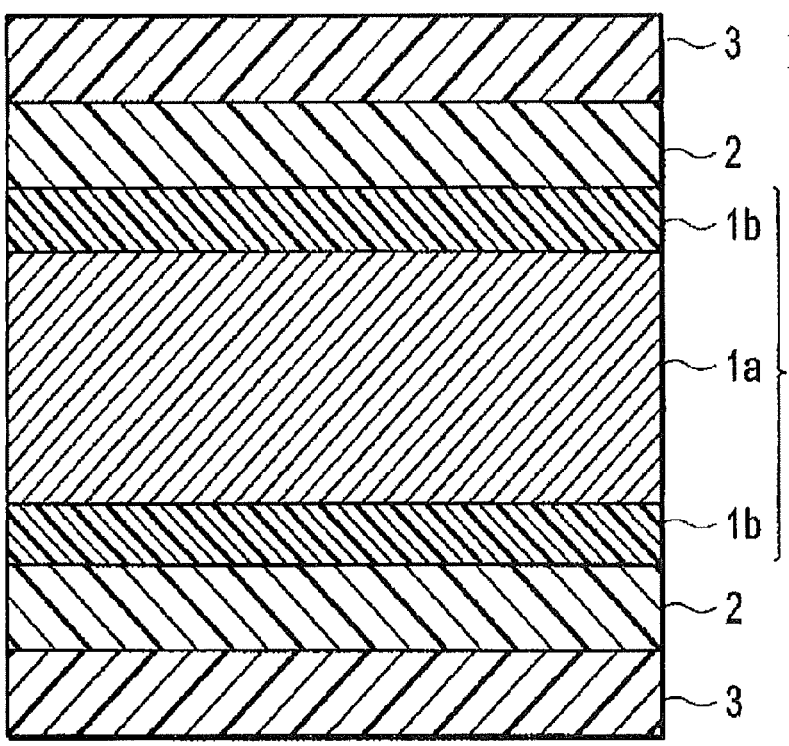
FIG. 1B is a partial sectional view schematically showing an alternative laminate structure of a surface according to an exemplary embodiment.

FIG. 1A is a partial sectional view schematically showing a laminate structure of the surface of a medical device having surface lubricity in wet state (hereinafter referred to simply as medical device) according to one exemplary embodiment (i.e., embodiment disclosed by way of example). FIG. 1B is a partial sectional view schematically showing an alternative laminate structure according to the surface of an exemplary embodiment. It will be noted that the respective reference numerals in FIGS. 1A and 1B indicate the following. Indicated by 1 is a base layer, by 1a is a core portion of the base layer, by 1b is a polymer surface layer, by 2 is a compound having a plurality of thiol groups in the molecule (thiol compound), by 3 is a surface lubricating layer, and by 10 is a medical device having surface lubricity in wet state, respectively.

As shown in FIGS. 1A and 1B, a medical device 10 of this embodiment includes a base layer 1 at least a surface of which is made of a polymer material, a compound (thiol compound) 2 supported on at least a part of the base layer 1 (in the figures, there is shown an example of being supported entirely on a surface of the base layer 1) and having a plurality of thiol groups in the molecule, and a surface lubricating layer 3 covering the compound 2 having a plurality of thiol groups in the molecule and made of a hydrophilic polymer having a reactive functional group, wherein the compound 2 having the thiol groups is supported (fixed) on the base layer 1 by irradiation of an ionized gas plasma and the surface lubricating layer 3 is bound to the base layer 1 through the thiol compound 2 by reaction between the compound 2 having the thiol groups and the hydrophilic polymer having the reactive functional group.

Each constituent member of the medical device of this embodiment is hereinbelow described in detail.

(1) Base Layer 1

The base layer 1 of an exemplary medical device can be such that at least a surface thereof is made of a polymer material.

(1a) Configuration of the Base Layer 1

With respect to the base layer 1, "at least a surface thereof is made of a polymer material" means that at least a surface of the base layer 1 can be constituted of a polymer material, not limited, in any way, to one wherein the base layer 1 is entirely (fully) constituted (formed) of a polymer material. Accordingly, as shown in FIG. 1B, the surface polymer layer 1b, which is formed by coating a surface of a base layer core portion 1a, which is formed of a hard reinforcing material such as a metal material, a ceramic material or the like, with a polymer material that is softer than the reinforcing material such as a metal material or the like by an appropriate method (a hitherto known method such as of dipping, spraying, coating/printing or the like), or by complexing (subjecting to an appropriate reaction treatment) the metal material or the like of the base layer core portion 1a and a polymer material of the surface polymer layer 1b, is also embraced within the base layer 1 of the disclosure here. Accordingly, the base layer core portion 1a can be in the form of a multi-layered structure wherein multiple layers of different types of materials are laminated, or a structure (composite body) wherein members formed of different types of materials for portions of a medical device are connected with one another. Moreover, a different type of middle layer (not shown) may be further formed between the base layer core portion 1a and the surface polymer layer 1b. Additionally, the surface polymer layer 1b may be in the form of a multi-layered structure wherein multiple layers of different types of polymer materials are laminated, or a structure (composite body) wherein members formed of different types of polymer materials for portions of a medical device are connected with one another.

(1b) Configuration of the Base Layer Core Portion 1a

No specific limitation is placed on the type of material usable for the base layer core portion 1a, and a reinforcing material capable of satisfactorily developing an optimal function as the base layer core portion 1a can be appropriately chosen depending on the application as a catheter, a guide wire, an indwelling needle or the like. For example, there can be exemplified various types of metal materials including a variety of stainless steels (SUS) such as SUS304, SUS316L, SUS420J2, SUS630 and the like, gold, platinum, silver, copper, nickel, cobalts, titanium, iron, aluminum and tin, alloys thereof such as nickel-titanium alloys, cobalt-chromium alloys, zinc-tungsten alloys and the like, inorganic materials such as various types of ceramic materials, and metal-ceramic composite materials although not limited thereto.

(1c) Configuration of the Base Layer 1 or the Surface Polymer Layer 1b

The polymer materials usable as the base layer 1 or surface polymer layer 1b are not specifically limited and include, for example, polyamide resins such as nylon 6, nylon 11, nylon 12, nylon 66 (all registered trade names) and the like, polyalkylene resins including polyethylene resins such as linear low-density polyethylene (LLDPE), low density polyethylene (LDPE), high-density polyethylene (HDPE) and the like and polypropylene resins, epoxy resins, urethane resins, diallylphthalate resins (allyl resins), polycarbonate resins, fluorine resins, amino resins (urea resins, melamine resins, benzoguanamine resins), polyester resins, styrol resins, acrylic resins, polyacetal resins, vinyl acetate resins, phenolic resins, vinyl chloride resins, silicone resins (silicon resins) and the like. These may be used singly or in combination of two or more. A most suited polymer material for an intended end usage as a polymer base of a catheter, a guide wire, an indwelling needle or the like can be appropriately chosen from the above polymer materials.

(1d) Configuration of a Middle Layer

For a material usable as the above middle layer (not shown), no limitation is placed specifically thereon, and proper selection is possible depending on the intended end usage. For example, there may be exemplified various types of metal materials, ceramic materials and organic-inorganic composite materials although not limited thereto. The "base layer 1 at least a surface of which is made of a polymer material" is referred to simply as "polymer base layer 1" or "base layer 1."

(2) Compound 2 Having a Plurality of Thiol Groups in the Molecule

The compound 2 having a plurality of thiol groups in the molecule (which may also be hereinafter referred to simply as "thiol compound") and constituting the medical device of this embodiment is supported on at least a portion of the surface of the polymer base layer 1.

The reason why the thiol compound 2 is supported on at least a portion of the surface of the base layer 1 is as follows: in the medical device for the intended end usage as a catheter, a guide wire, indwelling needle or the like, it is not always required that all the surfaces (entire surface) of these medical devices have lubricity in wet state, but it suffices that the thiol compound 2 is supported only on a surface portion (either a part or all), which is required to have surface lubricity in wet state.

It is noted here that the "support" means that the thiol compound 2 is fixed in a state of allowing the thiol compound 2 not to be readily released from the surface of the base layer 1, and may be in such a state that the thiol compound 2 is deposited on the surface of the base layer 1 or may be in a such a state that the thiol compound 2 is impregnated in the surface of the base layer 1.

The thiol compound 2 can be a compound having a plurality of thiol groups in the molecule. For example, the thiol compound 2 has such a structure that when it is strongly bound (fixed) to the surface of the base polymer 1 by reaction with a polymer material of the surface of the base layer 1 via plasma treatment and a subsequent thermal treatment, the residual thiol groups left on the outermost surface of the thiol compound 2 is likely to be exposed so as to permit easy reaction between the residual thiol groups and the reactive functional group of a hydrophilic polymer of the surface lubricating layer 3. From this standpoint, the thiol compound 2 is one having two or more thiol groups in one molecule (see, by comparison, FIG. 3 which is the results of the evaluation test of the surface lubrication retention of Example 1 having two or more thiol groups and FIG. 14 which is the results of the evaluation test of the surface lubrication retention of Comparative Example 7 having one thiol group), for example, 2 to 10 thiol groups in one molecule, for example, 3 to 6 thiol groups.

From this viewpoint, the thiol compounds may be any of linear, branched and cyclic compounds and can include, for example, compounds having two thiol groups in the molecule such as 1,2-ethandithiol, 1,2-propanedithiol, 1,3-propanedithiol, 1,4-butanedithiol, 2,3-butanedithiol, 1,5-pentanedithiol, 1,6-hexanedithiol, 1,8-octanedithiol, 3,6-dioxa-1,8-octanedithiol, bis(2-mercaptoethyl)ether, bis(2-mercaptoethyl)sulfide, 1,2-benzenedithiol, 1,4-benzenedithiol, 1,4-bis(mercaptomethyl)benzene, toluene-3,4-dithiol, 1,5-dimercaptonaphthalene, 2,6-dimercaptopurine, 4,4'-biphenyldithiol, 4,4'-thiobisbenzenethiol, tetraethylene glycol bis(3-mercaptopropionate) and the like, compounds having three thiol groups in the molecule such as 1,3,5-benzenetrithiol, tris-[(3-mercaptopropionyloxy)-ethyl]-isocyanurate (TEMPIC), triazinetrithiol, trimethylolpropanetris(3-mercaptopropionate) (TMMP) and the like, compounds having four thiol groups in the molecule such as pentaerythritoltetrakis(mercaptoacetate), pentaerythritoltetrakis(3-mercaptopropionate), pentaerythritoltetrakis(3-mercaptobutylate) and the like, compounds having six thiol groups in the molecule such as dipentaerythritolhexakis(3-mercaptopropionate) and the like, and derivatives and polymers thereof. These may be used singly or in combination of two or more. For example, mention is made of tris-[(3-mercaptopropionyloxy)-ethyl]-isocyanurate and dipentaerythritolhexakis(3-mercaptopropionate). These are compounds, which have such a structure wherein residual thiol groups are likely to be exposed on at the outermost surface so that the residual thiol groups and the reactive functional group of a hydrophilic polymer are likely to be reacted with each other when the thiol groups are bound to the surface of the base layer 1, and which also have a stable molecular skeleton and good affinity for the surface of the base layer 1 and have 3 to 6 thiol groups.

The thiol compounds are not limited to the above-exemplified compounds in any way, and other types of thiol compounds may also be usable if they can effectively develop effects similar to those described here.

(2a) Thickness of the Thiol Compound 2

The thickness of the thiol compound 2 constituting the medical device can be sufficient to allow a polymer material of the surface of the base layer 1 and the surface lubricating layer 3 to be strongly fixed together and excellent surface lubricity in use to be permanently shown. For example, the thickness is not larger than 10 µm, for example, not larger than 1 µm. If a thiol compound capable of effectively functioning as a so-called molecular adhesive is used, the thickness may be in a state of forming a monomolecular film layer (=One molecule of the thiol compound along a direction of thickness) of the thiol compound on the surface of the base layer 1. Moreover, from the standpoint that a smaller thickness of the thiol compound 2 leads to a finer medical device such as a catheter, a guide wire, an indwelling needle or the like, the thiol compound 2 may be in a state of being impregnated in the surface of the base layer 1.

(2b) Fixing Method of the Thiol Compound 2

With the medical device, the thiol compound 2 is fixed on the base layer 1 by irradiation of an ionized gas plasma (plasma treatment).

As a specific embodiment of fixing the thiol compound 2 on the base layer 1, mention is made of (i) an embodiment of supporting a compound having the thiol groups on the base layer by irradiating an ionized gas plasma on the surface of the base layer prior to coating of a solution dissolving the compound having the thiol groups onto the base layer surface. For example, prior to coating of a solution dissolving the thiol compound (thiol compound solution) onto the surface of the base layer 1 (prior to coating of the thiol compound), the surface of the base layer 1 is subjected to plasma treatment beforehand to modify and activate the surface. Thereafter, the thiol compound solution is coated so as to subject the thiol compound 2 and the surface of the base layer 1 to reaction (binding/fixing) with each other. The thiol compound 2 can be strongly fixed on the surface of the base layer 1. That is, for example, the thiol groups of the thiol compound 2 can react with a reactive functional group (including a functional group or a radical formed or introduced by the plasma treatment) such as an epoxy group, an isocyanate group or the like. However, if a thiol compound is coated merely on a surface of a base layer made of a polymer material having no such a reactive functional group (e.g. a polyamide or polyethylene), no reaction (binding) with a thiol compound takes place. Accordingly, the surface lubricating layer cannot be strongly fixed on the base layer through the thiol compound, permitting the surface lubricating layer to be peeled off. In contrast, according to an exemplary embodiment, when plasma treatment is carried out prior to coating of a thiol compound, there can be obtained such effects of improving and activating the surface of even a base layer made of a reactive functional group-free polymer material such as a polyamide or polyethylene and of improving wettability of the surface of the above base layer relative to the thiol compound solution. These effects enable the thiol compound solution to be uniformly coated onto the surface of the base layer or the thiol compound to be strongly bound (fixed) to the base layer.

In an exemplary embodiment, after coating of the thiol compound solution, heat treatment or the like may be carried out. By the heat treatment or the like after the coating of the thiol compound solution, the reaction between the surface of the base layer 1 and the thiol compound 2 can be facilitated or the thiol compound 2 per se can be polymerized. Thus, the heat treatment or the like ensures stronger fixing of the thiol compound on the base layer surface.

Further, mention is also made of (ii) another exemplary embodiment wherein the compound having the thiol groups is supported on the base layer by coating a solution dissolving the compound having the thiol groups onto a base layer surface and subsequently irradiating an ionized gas plasma thereon. For example, after the coating of the thiol compound solution onto the surface of the base layer 1 (after coating of the thiol compound), plasma treatment is carried out to have the thiol compound 2 and the surface of the base layer 1 react (bind) with each other. In this embodiment, ionized gas plasma irradiation enables strong fixing of the thiol compound 2 on the surface of the base layer 1.

In the embodiment of (ii) above, after the irradiation of an ionized gas plasma, heat treatment or the like may be carried out. By the heat treatment or the like after the plasma treatment, the reaction between the surface of the base layer 1 and the thiol compound 2 can be facilitated or the thiol compound 2 per se can be polymerized. Accordingly, stronger fixing of the thiol compound on the base layer surface is ensured.

Moreover, mention is made of a further exemplary embodiment of using plasma treatments prior to coating of the thiol compound of (i) and after coating of the thiol compound of (ii) in combination, i.e. (iii) an embodiment wherein an ionized gas plasma is irradiated onto the base layer surface, a solution dissolving the compound having the thiol groups is coated onto the base layer surface, and an ionized gas plasma is again irradiated thereon thereby supporting the compound having the thiol groups on the base layer. For example, the surface of the base layer 1 is subjected to plasma treatment prior to coating of the thiol compound to modify and activate the surface, after which the surface of the base layer 1 is coated with a thiol compound solution and is again subjected to plasma treatment to have the thiol compound 2 and the surface of the base layer 1 react (bind) with each other. This embodiment is excellent in that the thiol compound 2 can be very strongly fixed on the surface of the base layer 1 (see, by comparison, FIG. 8 which is the results of the evaluation test of the surface lubrication retention of Example 2 based on the embodiment of (iii) above and FIG. 10 which is the results of the evaluation test of the surface lubrication retention of Example 3 based on the embodiment of (ii) above).

Heat treatment or the like may be carried out after the plasma treatment has been effected again. Such a heat treatment enables the reaction between the surface of the base layer 1 and the thiol compound 2 to be facilitated or the thiol compound 2 per se to be polymerized. Accordingly, the heat treatment or the like ensures stronger fixing of the thiol compound on the surface of the base layer.

The effect of the plasma treatment in any of the embodiments (i) to (iii) resides in that the reaction of the thiol compound with a polymer material of the surface of the base layer 1 is facilitated. For example, plasma irradiation leads to generation and radiation of ionized ions or an electron beam, so that the bonds of the polymer material of the surface of the base layer 1 (such as, for example, a main chain of polymer) to be processed are cut off, or radicals generate, at which a thiol compound (thiol group) reacts. For example, cut-off or radical-generated sites are oxidized to introduce a reactive group such as a peroxide thereinto, with which the thiol compound can react (bind). In this way, the surface of the base layer 1 and the thiol compound 2 can be strongly fixed together. The embodiment of (iii) using the embodiments of (i) and (ii) in combination is described below.

(2b-1) Plasma Treatment Prior to Coating of a Thiol Compound

In an exemplary embodiment, an ionized gas plasma is preliminarily irradiated on the surface of the base layer 1 prior to coating of a thiol compound solution onto the base layer 1 (prior to coating of the thiol compound). In doing so, the surface of the base layer 1 is modified and activated and thus, wettability of the surface of the base layer 1 to the thiol compound solution can be improved, so that the thiol compound solution can be uniformly coated onto the surface of the base layer 1. The ionized gas plasma treatment may be carried out, to a desired extent, even against a fine and narrow inner surface of a medical device such as a catheter, a guide wire, an indwelling needle or the like Prior to preliminarily subjecting the surface of the base layer 1 to ionized gas plasma irradiation, the surface of the base layer 1 can be cleaned by an appropriate method. For example, it is desirable to eliminate oils and fats and dirt attached to the polymer material of the surface of the base layer 1 prior to enhancing the wettability of the surface of the base layer 1 by ionized gas plasma irradiation. It will be noted that in case where a thiol compound is coated without carrying out plasma treatment prior to the coating of a thiol compound as in the embodiment of (ii), the cleaning treatment can be carried out prior to the coating of the thiol compound solution.

The pressure conditions of the plasma treatment prior to the coating of a thiol compound can be either under reduced pressure conditions or under atmospheric pressure conditions. In view of the fact that a plasma gas can be irradiated from an arbitrary angle, no vacuum device is required and thus an apparatus can be made small in size, and a space-saving, low-cost system configuration can be realized and is thus excellent in economy, the treatment can carried out under atmospheric pressure conditions. When a plasma gas is irradiated while rotating once a plasma radiation nozzle around the periphery of an article to be treated, such as a guide wire, all periphery of the article can evenly, uniformly undergo the plasma treatment.

The ionized gas usable for the plasma treatment prior to coating of a thiol compound includes one or more gases composed of helium, neon, argon, krypton, air, oxygen, carbon dioxide, carbon monoxide, water vapor, nitrogen hydrogen or the like.

The irradiation time of the plasma treatment prior to coating of a thiol compound can be within a range of not greater than 10 minutes, for example, 0.1 second to 1 minute, for example, 1 to 40 seconds. The lower limit of the plasma irradiation time is not specifically limited. However, with a time of less than 0.1 second, there is concern that a difficulty is involved in securing a time sufficient to enhance the wettability (modification and activation) of the surface of the base layer 1 and that a difficulty is also involved in the formation of a very thin film (monomolecular film) of a thiol compound solution. On the other hand, if the plasma irradiation time exceeds 10 minutes, the activation of the surface of the base layer 1 becomes too far, so that there is concern that cutting off and re-combination (recombination of a molecular structure and crosslinkage) of the bonds of a polymer material of the surface of the base layer 1 generate excessively.

The temperature of an article to be treated in the plasma treatment prior to coating of a thiol compound (the base layer 1 prior to coating of a thiol compound) can be lower than a melting point of a polymer material of the surface of the base layer 1 and within a temperature range where the base layer 1 undergoes no deformation. In addition to a normal temperature, the plasma treatment may be carried out at a high temperature or low temperature created by heating or cooling. From an economic standpoint, a temperature (5 to 35° C.), not necessitating the use of a heating device or cooling device, can be used.

As the plasma treating conditions prior to coating of a thiol compound, it is sufficient to appropriately determine irradiation conditions including an applied current, a gas flow rate and the like depending on the area of an article to be treated, further the type of plasma irradiation apparatus and the type of ionized gas, and no specific limitation is placed thereon (see, for example, Example 1).

The plasma irradiation apparatus (system) usable for the plasma treatment prior to coating of a thiol compound is not specifically limited and includes, for example, a plasma irradiation apparatus (system) configured to include a plasma generating tube, into which gas molecules are introduced and excited therein to generate a plasma, and electrodes exciting the gas molecules in the plasma generating tube wherein the plasma is discharged from one end of the plasma generating tube although not limited to such a configuration (system) in any way. For example, from previously commercially sold ones, there may be used ionized gas plasma irradiation apparatus (systems) suited for irradiation on a catheter, a guide wire, an indwelling needle or the like, for example, an atmospheric-pressure plasma irradiation apparatus (system). For example, there can be used a plasma irradiation apparatus Duradyne (commercial name or trademark name), made by Tri-Star Technologies, a plasma irradiation apparatus Plasmabeam, made by Diener Electronic, and the like although not limited thereto in any way.

(2b-2) Coating of a Thiol Compound

The method of coating a thiol compound solution onto the polymer base layer 1 is not limited to a specific one, and hitherto known methods can be used including a coating/printing method (coating method), a dipping method (dipping method), a spray method (spraying method), a spin coating method, a mixed solution-impregnated sponge coating method and the like.

There is now described in detail an exemplary embodiment wherein the polymer base layer 1 is immersed in a thiol compound solution and dried to coat the thiol compound solution onto the surface of the polymer base layer 1, followed by plasma treatment and further by heat treatment to fix the thiol compound on the surface of the polymer base layer 1. In this regard, the disclosure here should not be construed as limited to these formation methods. It will be noted that with this embodiment, if the system is reduced in pressure for defoaming in a state of the polymer base layer 1 being immersed in the thiol compound solution, the solution can be quickly infiltrated into the fine, narrow inner surfaces of a medical device such as a catheter, a guide wire, an indwelling needle or the like thereby permitting the coating of the thiol compound 2 to be facilitated.

In case where the thiol compound 2 is fixed only on a part of the surface of the polymer base layer 1, the thiol compound solution is coated (immersed and dried) only onto a part of the polymer base layer 1, after which ionized gas plasma irradiation is again carried out, followed by heat treatment, if necessary, to enable the thiol compound 2 to be fixed to the desired surface portion of the polymer base layer 1.

If it is difficult to immerse only a part of the surface of the polymer base layer 1 in the thiol compound solution, the thiol compound 2 can be fixed on a desired surface portion of the base layer 1 by preliminarily protecting (covering) a surface portion of the polymer base layer 1, not to be formed with the thiol compound 2, with a detachable (attachable and detachable) appropriate member or material, subsequently immersing the base layer 1 in a thiol compound solution, drying, and again irradiating ionized gas plasma and carrying out heat treatment, if necessary, followed by removing the protecting member (material) from the surface portion of the polymer base layer 1 where the thiol compound 2 is not to be formed. In this regard, however, the method of the formation is not necessarily limited, but the thiol compound 2 can be fixed by conveniently using hitherto known methods. For example, if a difficulty is involved in immersing only a part of the base layer 1 in a thiol compound solution, other coating techniques (e.g. a coating method, a spray method or the like) may be applied to in place of the immersion method. Nevertheless, where both an outer surface and an inner surface of a cylindrical device are to have lubricity on both surfaces in wet state in view of the structure of the medical device 10 (see the configuration of FIGS. 1A and 1B), the immersion method (dipping method) is excellent in that both outer and inner surfaces can be coated at one time.

A thiol compound solution can be used for the formation of the thiol compound 2. In view of the formation of a uniform coating in a desired thickness, the concentration of a thiol compound in the thiol compound solution can be 0.001 to 20 wt %, for example, at 0.01 to 10 wt %. If the concentration of the thiol compound is less than 0.001 wt %, a satisfactory amount of the thiol compound cannot be fixed on the surface of the base layer 1, with some difficulty in that the surface lubricating layer 3 is strongly fixed on the base layer 1. On the contrary, where the concentration of the thiol compound exceeds 20 wt %, the viscosity of the thiol compound solution becomes too high, with concern that the thiol compound of a uniform thickness cannot be fixed and thus a difficulty may be involved in quickly coating a fine, narrow inner surface of a medical device such as a catheter, a guide wire, an injection needle or the like. In this regard, however, a concentration outside the above range may be adequately used if it is within a range not significantly influencing the effects of the medical device described here.

As a solvent used for the thiol compound solution, mention is made, for example, of water, alcohols such as methanol, ethanol, isopropanol, ethylene glycol and the like, ketones such as acetone, methyl ethyl ketone and the like, esters such as ethyl acetate and the like, halides such as chloroform and the like, olefins such as butane, hexane and the like, ethers such as tetrahydrofuran (THF), butyl ether and the like, aromatic compounds such as benzene, toluene and the like, and amides such as N,N-dimethylformamide (DMF) and the like although not limited thereto. These may be used singly or in combination of two or more.

The thiol compound solution can be subjected to drying conditions. For example, the medical device such as a catheter, a guide wire, an indwelling needle or the like, to which the disclosure here is directed, is so small that it does not take much drying time and thus, natural drying is enough. From this point of view, the drying conditions of the thiol compound solution include 20 to 150° C., for example, 20 to 130° C. and 1 second to 1 hour, for example, 1 to 30 minutes. If the drying time is smaller than 1 second, there is concern that because plasma treatment after coating of the thiol compound is carried out in an undried condition, the plasma energy is absorbed for the evaporation of a residual solvent and the like and thus, a difficulty is involved in satisfactorily activating the surface of the base layer 1 or the thiol compound (e.g. to enhance the surface energy of the base layer 1 and create functional groups (active points and sites) such as by excitation and ionization of the elements of the surface of the base layer 1 or the thiol compound). As a consequence, there is concern that it does not become possible to fully ensure the formation of binding portions with the surface of the base layer. On the other hand, when the drying time exceeds 1 hour, a further effect resulting from the drying over this time cannot be expected, thus being poor in economy.

The drying can be carried out under a normal (atmospheric) pressure and, besides, may be effected under increased pressure or reduced pressure.

As a drying means (apparatus), there can be used, for example, an oven, a reduced pressure drying machine and the like. With natural drying, no drying means (apparatus) is necessary.

(2b-3) Plasma Treatment after the Coating of a Thiol Compound

In an exemplary embodiment, after the coating of the thiol compound solution onto the surface of the base layer 1, ionized gas plasma irradiation is again conducted. Such a plasma treatment acts to activate the thiol compound 2 and the surface of the base layer 1 so that the thiol compound 2 and the surface of the base layer 1 are bound (reacted) together, thus enabling the thiol compound 2 to be strongly fixed. In addition, the thiol compound 2 per se can be polymerized by the plasma treatment.

The plasma treatment after the coating of the thiol compound of this embodiment can be carried out under the same conditions as the plasma treatment prior to the coating of the thiol compound by use of the same plasma irradiation apparatus as used for the plasma treatment prior to the coating of the thiol compound. It will be noted that although the plasma treatment conditions after the coating of the thiol compound of the embodiment can be such conditions within the exemplary ranges set out with respect to the plasma treatment prior to the coating of the thiol compound, there may not be required the same conditions as of the plasma treatment prior to the coating of the thiol compound.

(2b-4) Heat Treatment for Fixing the Thiol Compound 2

When the thiol compound 2 is fixed on the surface of the base layer 1, heat treatment or the like may be further carried out after the plasma treatment after the coating of the thiol compound thereby facilitating the reaction between the surface of the base layer 1 and the thiol compound 2 or promoting the polymerization of the thiol compound 2 per se.

Such a heat treatment can be one that is enough to facilitate the reaction (polymerization) of the thiol compound and can be appropriately determined depending on the temperature characteristics (heat resistance) of the polymer material of the surface of the base layer 1.

For example, the lower limit of the heat treating temperature (a set temperature of a heating apparatus such as a heating furnace) is at level not lower than a temperature capable of facilitating the reaction (polymerization) of a thiol compound, for example, not lower than 40° C., for example, not lower than 50° C. At temperatures lower than the temperature capable of facilitating the reaction (polymerization) of a thiol compound, a desired reaction may not proceed satisfactorily and it takes a long time for heat treatment, thus being poor in economy, or the reaction (polymerization) may not proceed by the heat treatment, with concern that a desired effect could not be obtained.

For example, the upper limit of the heat treatment temperature is at a level of not higher than a melting point minus 5° C. of a polymer material of the surface of the base layer 1, for example, not higher than a melting point minus 10° C. If the temperature is higher than a temperature of a melting point minus 5° C. of a polymer material of the surface of the base layer 1, the reaction (polymerization) is conveniently facilitated, with concern that the temperature may become higher than a set temperature although depending on the temperature distribution inside a heating apparatus such as a heating furnace or the like, so that part of the surface of the base layer 1 melts or undergoes deformation.

Exemplary polymer materials used as the surface of the base layer 1 and exemplary heat treating temperature ranges are disclosed below. The ranges of the heat treating temperature are not limiting. For example, where the polymer material of the surface of the base layer 1 is made of a variety of nylons (nylons 6, 11, 12, 66 and the like), the heat treatment temperature ranges 40 to 150° C., for example, 60 to 140° C. Where the polymer material of the surface of the base layer 1 is made of a variety of polyethylenes (LDPE, LLDPE, HDPE and the like), the heat treatment temperature ranges 40 to 85° C., for example, 50 to 80° C.

The heat treatment time can be one that is sufficient to facilitate the reaction (polymerization) of a thiol compound, and the heat treatment can be carried out for 15 minutes to 24 hours, for example, 30 minutes to 12 hours. If the heating time is less than 15 minutes, there is concern that the reaction (polymerization) does not proceed satisfactorily, an amount of an unreacted thiol compound increases and the effects of securing the binding portion with the surface of the base layer 1 and reinforcing strength through the polymerization of the thiol compound 2 per se cannot satisfactorily develop. On the other hand, where the heating time exceeds 24 hours, a further effect of the heating over the above time cannot be obtained, thus being poor in economy.

In this regard, however, with respect to the heat treatment temperature and time, where the plasma treatment after coating of a thiol compound is effected, for example, under vacuum, the temperature of an article to be treated rises during the plasma treatment and thus, such a reaction (polymerization) as in the heating treatment occurs during the plasma treatment. Thus, they can be determined while taking the plasma treating conditions into consideration.

The heat treatment can be effected under a normal pressure (atmospheric pressure) and besides, may be carried out under increased pressure or reduced pressure.

Where a thiol compound per se is polymerized, the polymerization can be promoted by adding, to a thiol compound solution, an additive such as a thermal polymerization initiator in an appropriate amount on a timely basis. As a heating means (apparatus), there can be utilized, for example, an oven, a dryer, a microwave heating apparatus and the like.

Methods other than the heat treatment for promoting the reaction or polymerization of a thiol compound, mention is made, for example, UV irradiation, electron beam irradiation and the like although not limited thereto.

After fixing of the thiol compound 2, it is possible to leave only the thiol compound bound on the surface of the polymer base layer 1 by cleaning the residual thiol compound with an appropriate solvent.

(3) Surface Lubricating Layer 3

The surface lubricating layer 3 constituting the medical device of this embodiment is made of a hydrophilic polymer covering the surface of the thiol compound 2 and having a reactive functional group.

The hydrophilic polymer forming the surface lubricating layer 3 and having a reactive functional group (which is hereinafter referred to simply as "hydrophilic polymer") can be formed sufficiently to cover the surface (entirety) of the thiol compound 2. In this regard, however, where the thiol compound 2 is formed over the entire surface of the base layer 1 including a surface portion which is required to have surface lubricity in wet state, the surface lubricating layer 3 may be formed only at the surface portion (which may be a part or a whole) required to have surface lubricity in wet state of the surface of the thiol compound 2.

(3a) Thickness of the Surface Lubricating Layer 3

The surface lubricating layer 3 constituting the medical device of the embodiment can have a thickness enough to permanently show excellent surface lubricity in use and thus, no specific limitation is placed thereon. The thickness of the surface lubricating layer 3 in non-swollen state can be 0.5 to 5 µm, for example, 1 to 5 µm, for example, 1 to 3 µm. If the thickness of the surface lubricating layer 3 in non-swollen state is less than 0.5 µm, it is difficult to form a uniform film, with the possibility that surface lubricity in wet state is not satisfactorily shown. On the other hand, when the thickness of the surface lubricating layer 3 in non-swollen state exceeds 5 µm, there is concern that when medical device 10 is inserted into the blood vessel within a living body, swelling of such a thick surface lubricating layer may lead to the damage of the inner tissue of the vessel or the like, or is unlikely to permit passage of the medical device upon passage through a site (e.g. an interior of peripheral vessel or the like) wherein a clearance between the vessel or the like and the medical device is small.

(3b) Hydrophilic Polymer

The hydrophilic polymer forming the surface lubricating layer 3 and having a reactive functional group can be obtained, for example, by copolymerization of a monomer having a reactive functional group in the molecule and a hydrophilic monomer.

(3b-1) Monomer Having a Reactive Functional Group

As such a monomer having a reactive functional group, no limitation is placed thereon so far as it has reactivity with a thiol group. Mention is made, for example, of monomers having epoxy group such as glycidyl acrylate, glycidyl methacrylate and the like, and monomers having an isocyanate group in the molecule, such as acryloyloxyethylisocyanate. Of these, monomers having an epoxy group, such as glycidyl acrylate, glycidyl methacrylate and the like, can be used because they have, as a reactive functional group, an epoxy group that is excellent in reactivity with a thiol group, the reaction is promoted by application of heat, a crosslinked structure is formed and thus becomes insolubilized to easily form a surface lubricating layer, and handling is relatively easy. The hydrophilic polymer making use of the monomer having the epoxy group is gentler in reaction rate (appropriate in rate) in the course of the reaction under heating operations (under heat treatment) than hydrophilic polymers making use of monomers having an isocyanate group in the molecule. Accordingly, because the reaction rate is so gentle (appropriate in rate) as to suppress or control the lowering of lubricity ascribed to the rise of a crosslinking density of the surface lubricating layer after gelation or solidification by immediate reaction in the course of the reaction such as under heating operations or reaction with a thiol compound or mutual crosslinking reaction between reactive functional groups, handleability is considered as good. The monomers having these reactive functional group may be used singly or in combination of two or more.

(3b-2) Hydrophilic Monomer

As a hydrophilic monomer, any one may be used so far as it develops lubricity in a body fluid or an aqueous solvent and thus, no limitation is placed thereon. Mention can be made, for example, of acrylamide and derivatives thereof, vinyl pyrrolidone, acrylic acid or methacrylic acid and derivatives thereof, and monomers having a sugar or phospholipid at a side chain. Examples include N-methylacrylamide, N,N-dimethylacrylamide, acrylamide, acryloyl morpholine, N,N-dimethylaminoethyl acrylate, vinyl pyrrolidone, 2-methacryloyloxyethylphosphoryl choline, 2-methacryloyloxyethyl-D-glycoside, 2-methacryloyloxyethyl-D-mannoside, vinyl methyl ether, hydroxyethyl methacrylate and the like. From the standpoint of the ease in synthesis and operability, N,N-dimethylacrylamide can be used. The hydrophilic monomers may be used singly or in combination of two or more.

(3b-3) Preferred Form of a Hydrophilic Polymer

In order to develop good lubricity, block or graft copolymers can be used wherein the molecules of a monomer having a reactive functional group gather together to form a reactive domain and the molecules of a hydrophilic monomer gather together to form a hydrophilic domain. Using such a block or graft copolymer, good results are obtained with respect to the strength and lubricity of the resulting surface lubricating layer.

No limitation is placed on the method of preparing (method of polymerizing) these hydrophilic polymers, and the preparation is possible by application, for example, of hitherto known polymerization methods such as a living radical polymerization method, a polymerization method using a macromonomer, a polymerization method using a polymer initiator such as a macro azo initiator or the like, a polycondensation method and the like.

(3c) Formation Method of the Surface Lubricating Layer 3 (Binding Forms of Between the Base Layer 1-the Surface Lubricating Layer 3)

An exemplary embodiment can include the aforementioned base layer 1, thiol compound 2 and surface lubricating layer 3, wherein, as stated hereinbefore, the thiol compound 2 is fixed on the base layer 1 by irradiation of an ionized gas plasma and the surface lubricating layer 3 is bound to the base layer 1 through the reaction between the residual thiol group of the thiol compound and the reactive functional group of the hydrophilic polymer.

Where the surface lubricating layer 3 is formed, the base layer 1, to which the thiol compound 2 has been fixed, can be immersed in a solution dissolving a hydrophilic polymer (hereinafter referred to simply as "hydrophilic polymer solution"), dried and thermally treated. By this, the reactive functional group (e.g. an epoxy group) of the hydrophilic polymer and the residual thiol group of the thiol compound 2 are reacted, thereby enabling the surface lubricating layer 3 to be bound (fixed) to the base layer 1 simultaneously with the formation of the surface lubricating layer 3. It will be noted that if the system is reduced in pressure for defoaming in a state of immersing the base layer 1, fixed with the thiol compound 2, in a hydrophilic polymer solution, the formation of the surface lubricating layer 3 can be facilitated by quickly impregnating the solution in a fine narrow inner surface of the medical device such as a catheter, a guide wire, an injection needle or the like.

For example, it will also be noted that where the surface lubricating layer 3 is formed only at part of the thiol compound 2, only the part of the thiol compound 2, fixed on the base layer 1, is immersed in the hydrophilic polymer solution and subjected to heat treatment or the like, thereby enabling the surface lubricating layer 3 made of the hydrophilic polymer to be formed on a desired surface portion of the thiol compound 2.

If it is difficult to immerse only a part of the thiol compound 2, fixed on the base layer 1, in a hydrophilic polymer solution, the thiol compound 2 fixed on the base layer 1 can be immersed in the hydrophilic polymer solution after preliminary protection (coverage) of the surface portion of the thiol compound 2, on which the surface lubricating layer 3 is not to be formed, with a detachable (attachable or detachable) member or material. Thereafter, the protecting member (material) on the surface portion of the thiol compound 2, which is not to be formed with the surface lubricating layer 3, can be removed and subsequently subjected to heat treatment or the like, thereby forming the surface lubricating layer 3 made of a hydrophilic polymer on a desired surface portion of the thiol compound 2. In this regard, however, the disclosure is not limited to these formation methods, but the surface lubricating layer 3 can be formed by appropriately using hitherto known methods.

It will be noted that in place of the method of immersing the base layer 1, fixed with the thiol compound 2, in the above hydrophilic polymer solution (immersing method or dipping method), there can be applied conventionally known methods including, for example, a coating/printing method, a spray method (spraying method), a spin coating method, a mixed solution impregnated sponge coating method and the like.

As a procedure of reaction between a thiol compound and a hydrophilic polymer, conventionally known methods can be applied including, for example, heat treatment, light irradiation, electron beam irradiation, radiation irradiation and the like.

An exemplary embodiment taken by way of example is described in detail wherein the thiol compound 2, fixed on the base layer 1, is immersed in a hydrophilic polymer solution to coat (cover) the surface of the thiol compound 2 with the hydrophilic polymer solution (coating solution), followed by heating operations to cause the residual thiol group of the thiol compound to react with the reactive functional group of the hydrophilic polymer thereby forming the surface lubricating layer 3. In this connection, however, the disclosure should not be construed as limited to these coating and reaction treatment operations in any way.

(3c-1) Concentration of the Hydrophilic Polymer Solution

A hydrophilic polymer solution can be used for the formation of the surface lubricating layer 3. From the standpoint of a uniform coating in a desired thickness, the concentration of the hydrophilic polymer in the hydrophilic polymer solution can be at 0.1 to 20 wt %, for example, 0.5 to 15 wt %, for example, 1 to 10 wt %. If the concentration of the hydrophilic polymer solution is less than 0.1 wt %, there is concern that the immersion operation has to be repeated plural times so as to obtain a surface lubricating layer 3 of a desired thickness, resulting in a low production efficiency. On the other hand, when the concentration of the hydrophilic polymer solution exceeds 20 wt %, there is also concern that the viscosity of the hydrophilic polymer solution becomes too high to coat a uniform film and that a difficulty is involved in quickly coating a fine, narrow inner surface of a medical device such as a catheter, a guide wire, an injection needle or the like. In this regard, however, the concentration outside the above range may be adequately usable so far as it is within a range not influencing the effects achieved here.

(3c-2) Solvent Used for the Hydrophilic Polymer Solution

The solvents used for dissolution of a hydrophilic polymer solution include, for example, N,N-dimethylformamide (DMF), chloroform, acetone, tetrahydrofuran (THF), dioxane, benzene and the like although not limited thereto. These may be used singly or in combination of two or more.

(3c-3) Reaction Conditions (Heating Conditions) for Forming the Surface Lubricating Layer 3

The surface lubricating layer 3 can be bound to the base layer 1 by reaction between the reactive functional group (e.g. an epoxy group) of the hydrophilic polymer and the residual thiol group of the thiol compound 2 such as by heat treatment upon formation of the surface lubricating layer 3.

Such heat treatment conditions (reaction conditions) may be those capable of causing (promoting) the reaction between the reactive functional group of the hydrophilic polymer and the residual thiol group of the thiol compound 2 and can be appropriately determined depending on the temperature characteristics (heat resistance) of the polymer material of the surface of the base layer 1.

For example, the lower limit of the heat treatment temperature (a set temperature of a heating apparatus such as a heating furnace) is at a level capable of promoting the reaction between the reactive functional group of the hydrophilic polymer and the residual thiol group of the thiol compound 2, for example, not lower than 40° C., for example, not lower than 50° C. At temperatures lower than those capable of promoting the reaction between the reactive functional group of the hydrophilic polymer and the residual thiol group of the thiol compound 2, a desired reaction cannot be promoted satisfactorily and it takes a long time for the heat treatment, resulting in poor economy, or a desired reaction does not proceed by the heat treatment, with concern that an intended effect is not obtained.

For example, the upper limit of the heat treatment temperature is at not higher than a melting point minus 5° C. of a polymer material of the surface of the base layer 1, for example, not higher than a melting point minus 10° C. With temperatures higher than a melting point minus 5° C. of a polymer material of the surface of the base layer, although a desired reaction proceeds satisfactorily, the treatment temperature may rise over a set temperature although depending on a temperature distribution inside a heating apparatus such as a heating furnace, with concern that part of the surface of the base layer 1 melts or undergoes deformation.

Exemplary polymer materials used as the surface of the base layer 1 and exemplary ranges of heat treatment temperatures are disclosed below. The ranges of the heat treatment temperature are not limiting. For example, where the polymer materials of the surface of the base layer 1 are made of various types of nylons (nylons 6, 11, 12, 66 and the like), the heat treatment temperatures are at 40 to 150° C., for example, at 60 to 140° C. Where the polymer materials of the surface of the base layer 1 are made of various types of polyethylenes (LDPE, LLDPE, HDPE and the like), the heat treatment temperatures are at 40 to 85° C., for example, at 50 to 80° C.

The heat treatment time may be one capable of promoting the reaction between the reactive functional group of the hydrophilic polymer and the residual thiol group of the thiol compound 2 and is not specifically limited, and is at 15 minutes to 15 hours, for example, at 30 minutes to 10 hours. If the heating time is less than 15 minutes, the reaction scarcely proceeds, with concern that an unreacted hydrophilic polymer increases in amount and also with the possibility that a difficulty is involved in keeping the surface lubricity over a long time. On the other hand, where the heating time exceeds 15 hours, a further effect ascribed to the heating is not obtained, thus being poor in economy.

No limitation is placed on the pressure conditions at the time of the heat treatment, and the treatment may be carried out not only under a normal pressure (atmospheric pressure), but also under increased pressure or under reduced pressure. Where the reactive functional group of a hydrophilic polymer is an epoxy group, a reaction catalyst such as a trialkylamine compound or a tertiary amine compound such as pyridine or the like may be added to a hydrophilic polymer solution timely in an appropriate amount so as to promote the reaction with the residual thiol group of the thiol compound 2. For a heating means (apparatus), there can be utilized, for example, an oven, a dryer, a microwave heating apparatus and the like.

Aside from the heat treatment, the methods of promoting the reaction between the reactive functional group of a hydrophilic polymer and the residual thiol group of the thiol compound 2 include, for example, the use of light, an electron beam, a radiation and the like, although not limited thereto in any way.

After the formation of the surface lubricating layer 3, an excess hydrophilic polymer may be cleaned with an appropriate solvent thereby permitting the hydrophilic polymer alone, where the surface lubricating layer 3 is strongly fixed on the base layer 1, to be left thereat.

The thus formed surface lubricating layer 3 develops lubricity after absorption of water at a body temperature of a patient (30 to 40° C.).

(4) Utility of the Medical Device 10

The medical device 10 having surface lubricity in wet state can be used in contact with a body fluid or blood, has surface lubricity in an aqueous liquid such as a body fluid, a physiological saline solution or the like, and can improve workability and reduce damages of tissues and mucosa membranes. Specific examples include catheters, guide wires, indwelling needles and the like used in blood vessels. Besides, the following medical devices can be indicated.

(4a) Catheters to be perorally or pernasally inserted or indwelled in digestive organs such as gastric catheters, nutrition catheters, tubes for tubal feeding and the like.

(4b) Catheters to be perorally or pernasally inserted or indwelled in the respiratory tract or windpipe such as oxygen catheters, oxygen canulas, tubes or cuffs for endotracheal tube, tubes or cuffs for tracheostomy tube, endotracheal suctioning catheters and the like.

(4c) Catheters to be inserted or indwelled in the urethral tube or urinary duct such as urethral catheters, urinary catheters, catheters or balloons for urethral balloon catheters and the like.

(4d) Catheters to be inserted or indwelled in various body cavities, organs and tissues, such as suction catheters, drain catheters, rectal catheters and the like.

(4e) Catheters to be inserted or indwelled in blood vessels, such as indwelling needles, IVH catheters, thermodilution catheters, angiographic catheters, vasodilation catheters and dilators or introducers and the like, or guide wires, stylets and the like for these catheters.

(4f) Artificial windpipes, artificial bronchial tubes and the like.

(4g) Medical devices for extracorporeal circulation therapy (artificial lung, artificial heart, artificial kidney and the like) and circuits thereof.

EXAMPLES

Example 1

Base Material: Nylon 12

After ultrasonic cleaning of a nylon 12 (Grilamid L16, made by EMS) sheet (30 mm long×50 mm wide×1 mm thick, polymer base layer 1) in acetone, a plasma irradiation apparatus (Duradyne, PT-2000P, made by Tri-Star Technologies) was attached with 1 inch wide nozzle, followed by argon ion gas plasma irradiation on the entire surface of the nylon 12 sheet from a distance of 10 mm for 25 seconds under conditions of an atmospheric pressure, a gas flow of 15 SCFH and a plasma current of 2.00 A (plasma treatment prior to coating of a thiol compound).

The nylon 12 sheet, which had been subjected to the plasma treatment prior to coating of a thiol compound, was immersed in a DMF solution of tris-[(3-mercaptopropionyloxy)-ethyl]-isocyanurate (TEMPIC) (made by SC Organic Chemical Co., Ltd.) (three thiol groups in one molecule) whose concentration was adjusted to 20 mM and was naturally dried for 10 minutes. Thereafter, using the plasma irradiation apparatus, argon ion gas plasma irradiation was again carried out for 25 seconds under the same conditions as indicated above (plasma treatment after the coating of the thiol compound). Subsequently, TEMPIC was fixed on the surface of the nylon 12 sheet by heat treatment in an oven of 130° C. for 3 hours. Moreover, the nylon 12 sheet, fixed with TEMPIC thereon, was subjected to ultrasonic cleaning in DMF to remove excess TEMPIC not fixed to the sheet surface. In doing so, the thiol compound 2 covering the entire surface of the base layer 1 (nylon 12 sheet) and made of TEMPIC was formed (fixed).

After immersion of the TEMPIC-fixed nylon 12 sheet in a DMF solution (block copolymer solution) of a block copolymer having N,N-dimethylacrylamide (DMAA) as a hydrophilic domain and glycidyl methacrylate (GMA) as a reactive domain (DMAA:GMA (molar ratio)=11.5:1) dissolved at a rate of 5 wt %, followed by reaction in an oven of 130° C. for 10 hours to form a surface lubricating layer 3 having a thickness (in non-swollen state) of 2 μm and made of the above block copolymer (hydrophilic polymer) in such a way as to cover the surface of the thiol compound 2 fixed on the surface of the base layer 1 (nylon 12 sheet) and made of TEMPIC.

Figure 2A:
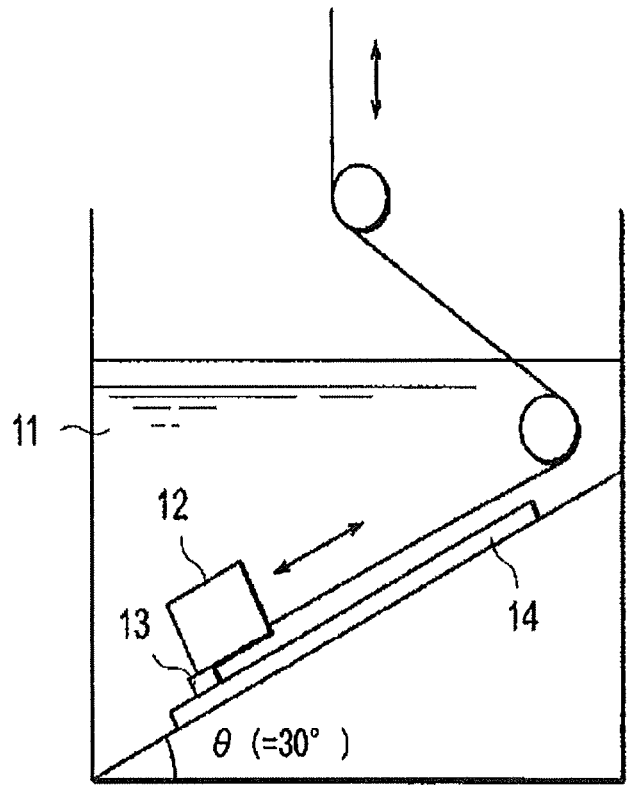
FIG. 2A is a schematic view of an exemplary testing apparatus for evaluating surface lubrication retention used in Example 1 and Comparative Examples 1 to 4.
Figure 2B:
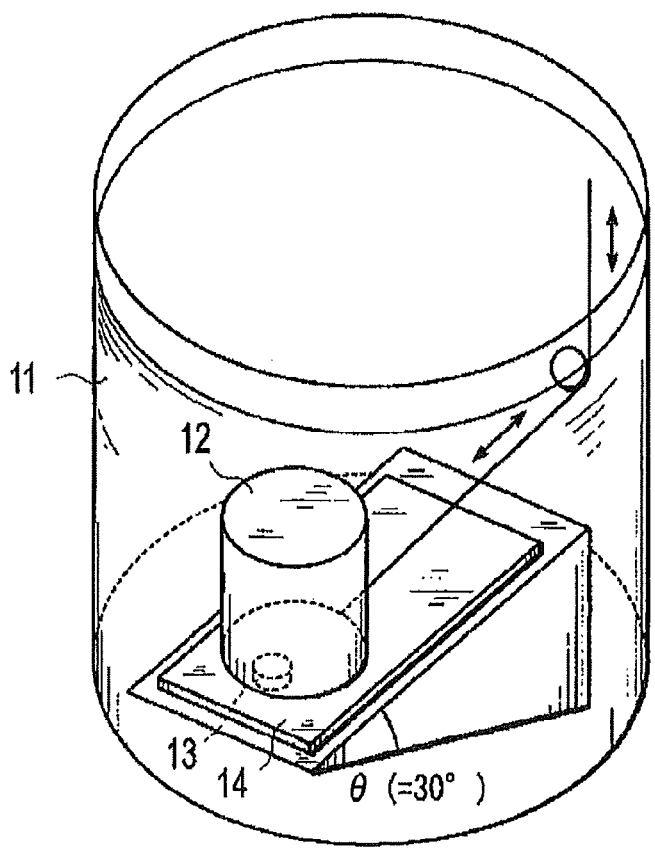
FIG. 2B is a perspective view of the exemplary testing apparatus for evaluating surface lubrication retention shown in FIG. 2A.

The sheet (sample) 14 wherein the surface lubricating layer 3 had been formed according to the above procedure was fixed on a plate inclined at an angel of 30° in water 11 as shown in FIGS. 2A and 2B. A cylindrical brass weight 12 of 1 kg, to which a cylindrical polyethylene sheet 13 (φ10 mm, R 1 mm) was attached, was gently placed on the surface lubricating layer 3 of the sheet (sample) 14. In this condition, the weight 12 was reciprocated 300 times up and down at a rate of 100 cm/minute at width intervals of 2 cm. The maximum friction resistance value in the respective reciprocating cycles was measured by autograph (AG-IS10 kN, made by Shimadzu Corporation) to check the surface lubrication retention relative to 300 cycles of repeated sliding.

Figure 3:
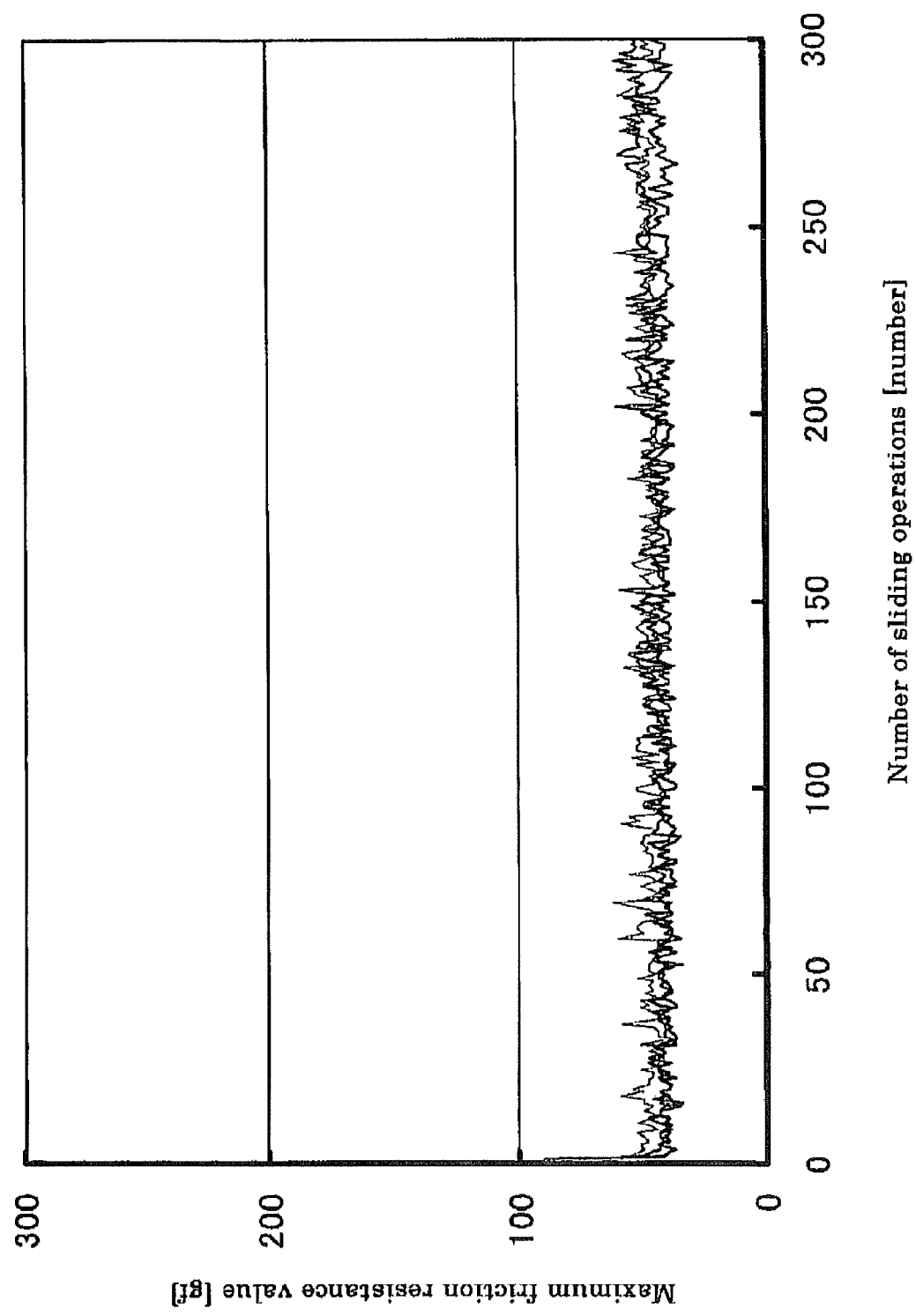
FIG. 3 is a graph showing the results of the evaluation test of the surface lubrication retention of a sheet (sample) of an exemplary medical device having surface lubricity in wet state obtained in Example 1.

As a result of the test, the maximum friction resistance values were constant as shown in FIG. 3 and thus, stable lubricity was shown in the 300 cycles of repeated sliding.

It will be noted that in FIG. 3, three samples were similarly tested and the respective results are shown. In the following FIGS. 4 to 14, three samples were tested in a similar way and the respective results are shown.

Comparative Example 1

Base Material: Nylon 12

After ultrasonic cleaning of such a nylon 12 sheet (polymer base layer 1) as used in Example 1 in acetone, the sheet was immersed in the same block copolymer solution as in Example 1, followed by reaction in an oven of 130° C. for 10 hours to form a surface lubricating layer 3 having a thickness (in non-swollen state) of 2 μm and made of the above block copolymer (hydrophilic polymer) so as to cover the surface of the base layer 1 (nylon 12 sheet).

Figure 4:
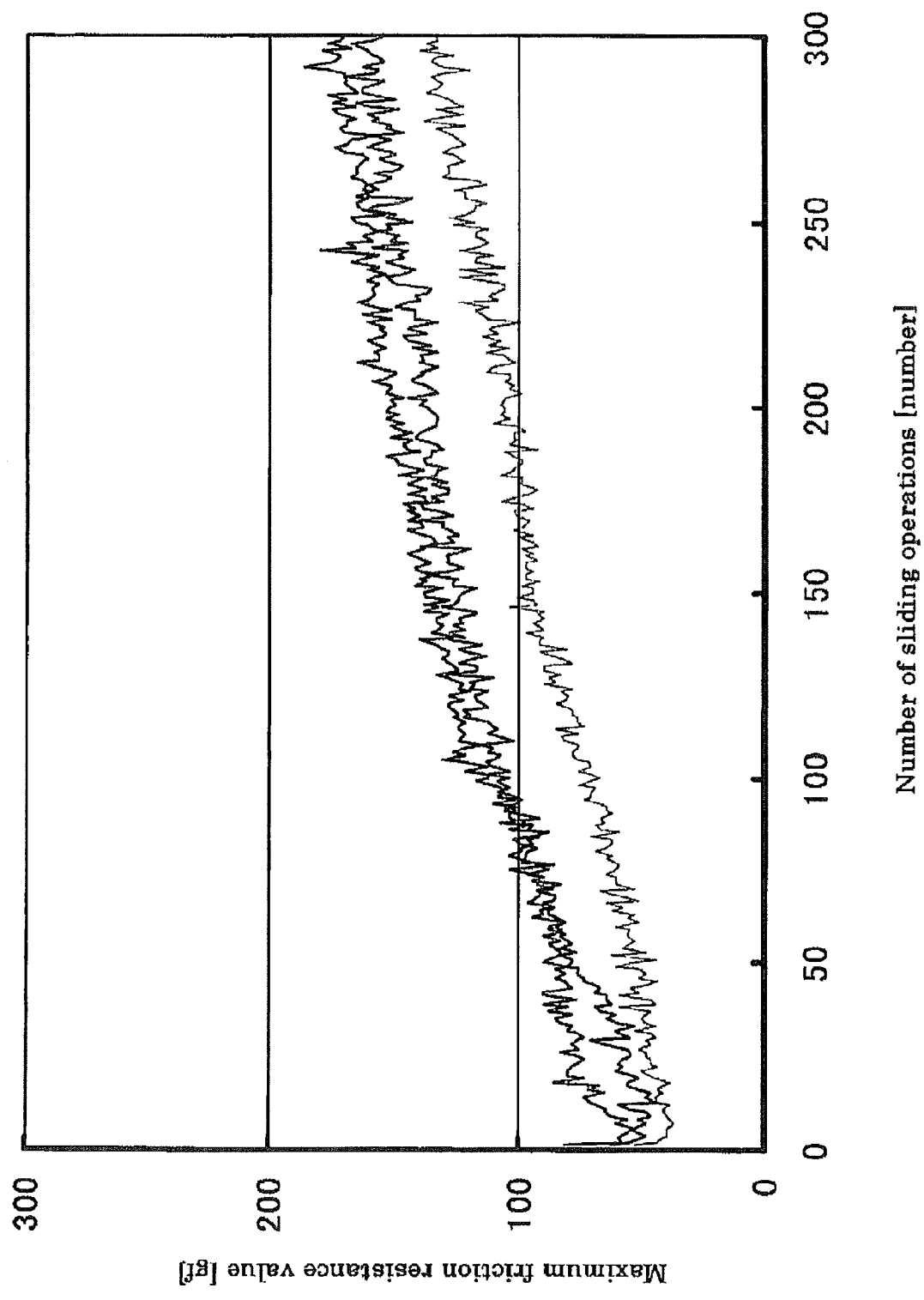
FIG. 4 is a graph showing the results of the evaluation test of the surface lubrication retention of a sheet (sample) of an exemplary medical device having surface lubricity in wet state obtained in Comparative Example 1.

Thereafter, in the same manner as in Example 1, the surface lubrication retention of the sheet (sample), on which the surface lubricating layer 3 was formed according to the above procedure, was checked, revealing that although low friction resistance values were initially shown as in FIG. 4, the friction resistance values gradually increased during repetitions of sliding, thus the persistence as the surface lubricating layer being poor.

Comparative Example 2

Base Material: Nylon 12

A nylon 12 sheet (polymer base layer 1) as used in Example 1 was subjected to ultrasonic cleaning in acetone, and using the same plasma irradiation apparatus as in Example 1, argon ion gas plasma irradiation was effected for 25 seconds under the same conditions as in Example 1, followed by immediate immersion in such a block copolymer solution as in Example 1 and reaction in an oven of 130° C. for 10 hours to form a surface lubricating layer 3 having a thickness (in non-swollen state) of 2 μm and made of the above block copolymer (hydrophilic polymer) so as to cover the surface of the base layer 1 (nylon 12 sheet).

Figure 5:
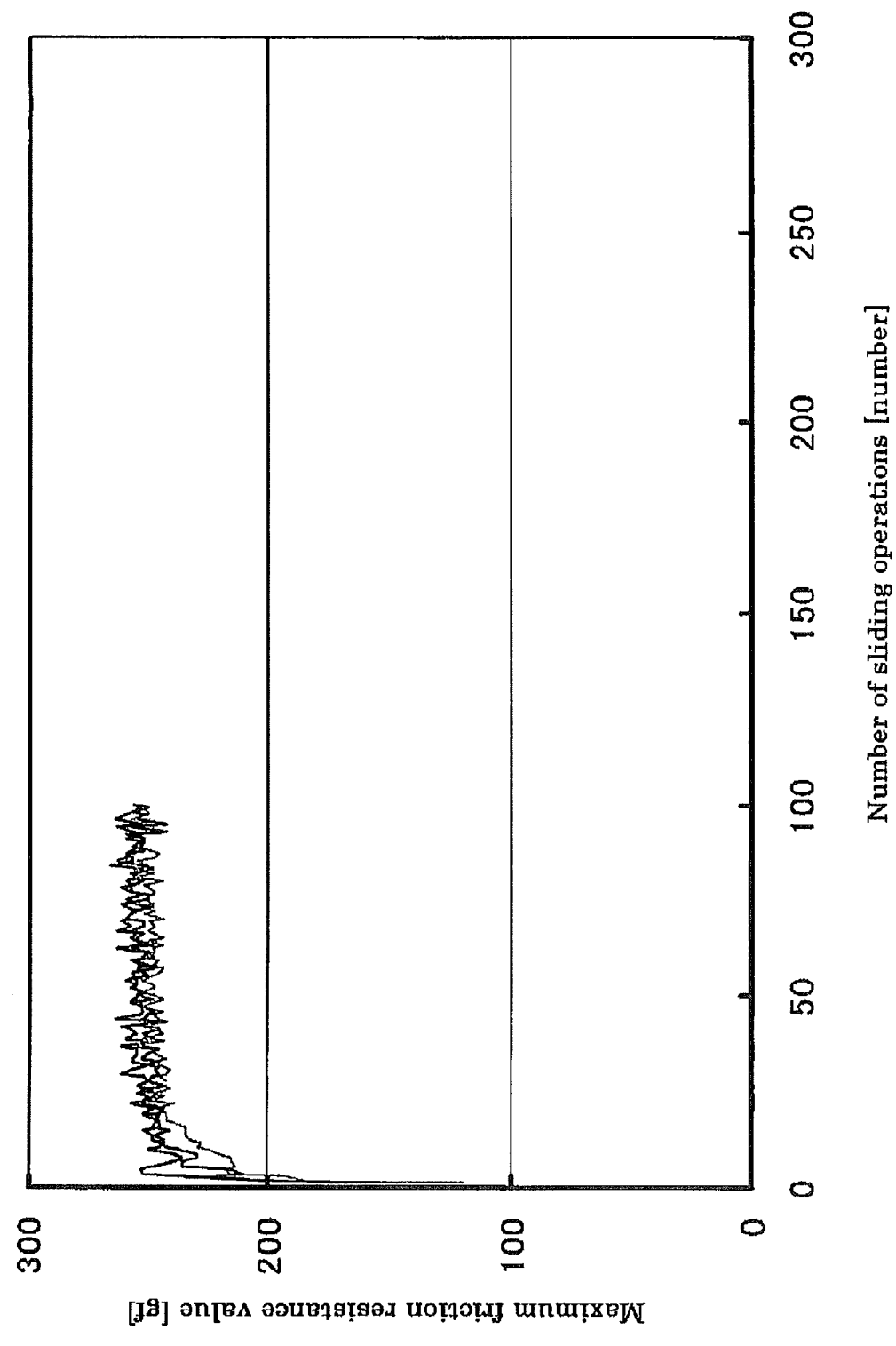
FIG. 5 is a graph showing the results of the evaluation test of the surface lubrication retention of a sheet (sample) of an exemplary medical device having surface lubricity in wet state obtained in Comparative Example 2.

Thereafter, in the same manner as in Example 1, the surface lubrication retention of the sheet (sample), on which the surface lubricating layer 3 was formed according to the above procedure, was checked, revealing that the friction resistance values increased after several siding cycles shown as in FIG. 5 and thus, the persistence as a surface lubricating layer was poor. Hence, in the test using the sheet (sample) of this Comparative Example 2, the surface lubrication retention was checked only up to 100 cycles of repeated sliding.

Comparative Example 3

Base Material: Nylon 12

A nylon 12 sheet (polymer base layer 1) as in Example 1 was subjected to ultrasonic cleaning in acetone, immersed in a DMF solution of TEMPIC whose concentration was adjusted to 20 mM and dried, followed by heating in an oven of 130° C. for 3 hours to fix TEMPIC on the surface of the nylon 12 sheet. Thereafter, excess TEMPIC, which was not fixed on the sheet surface, was removed by ultrasonic cleaning in DMF. In this way, the thiol compound 2 made of TEMPIC was formed (fixed) as covering the entire surface of the base layer 1 (nylon 12 sheet).

The TEMPIC-fixed nylon 12 sheet was immersed in a block copolymer solution as used in Example 1, followed by reaction in an oven of 130° C. for 10 hours to form a surface lubricating layer 3 having a thickness (in non-swollen state) of 2 μm and made of the above block copolymer (hydrophilic polymer) so as to cover the surface of the thiol compound 2 made of TEMPIC and fixed on the surface of the base layer 1 (nylon 12 sheet).

Figure 6:
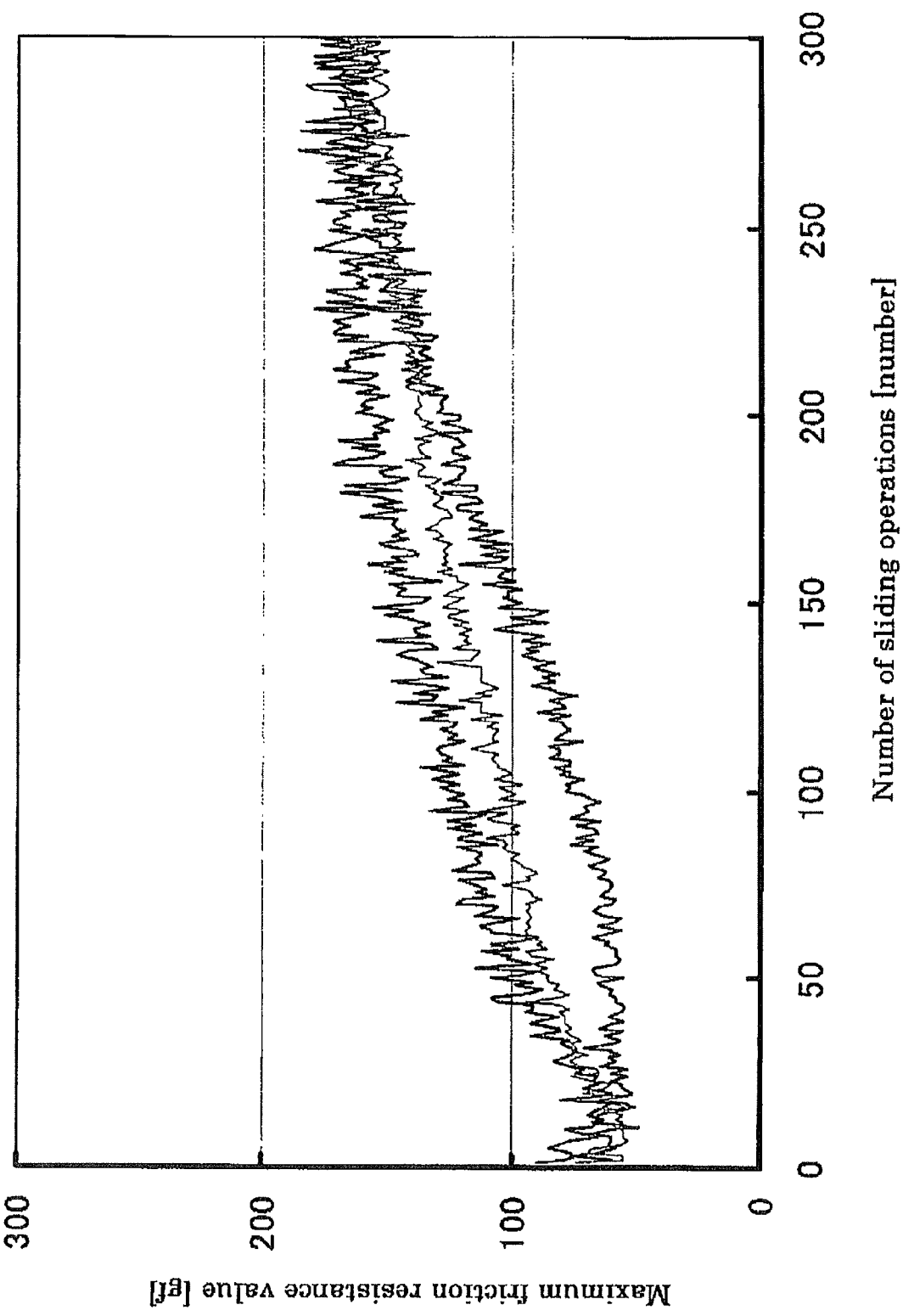
FIG. 6 is a graph showing the results of the evaluation test of the surface lubrication retention of a sheet (sample) of an exemplary medical device having surface lubricity in wet state obtained in Comparative Example 3.

Thereafter, in the same manner as in Example 1, the surface lubrication retention of the sheet (sample) having the surface lubricating layer 3 formed according to the above procedure was checked, revealing that although low friction resistance values were initially shown as in FIG. 6, the friction resistance values gradually increased during repetitions of sliding, thus being poor in persistence as a surface lubricating layer.

Comparative Example 4

Base Material: Nylon 12

The procedure of Example 1 was repeated except that TEMPIC of Example 1 was changed to L-cysteine hydrochloride (Wako Pure Chemical Industries, Ltd.) (one thiol group, one amino group and one carboxyl group in one molecule), thereby forming a surface lubricating layer 3 made of the block copolymer (hydrophilic polymer) and having a thickness (in non-swollen state) of 2 μm so as to cover the thiol compound 2 fixed on the surface of the base layer 1 (nylon 12 sheet) and made of the L-cysteine hydrochloride.

Figure 7:
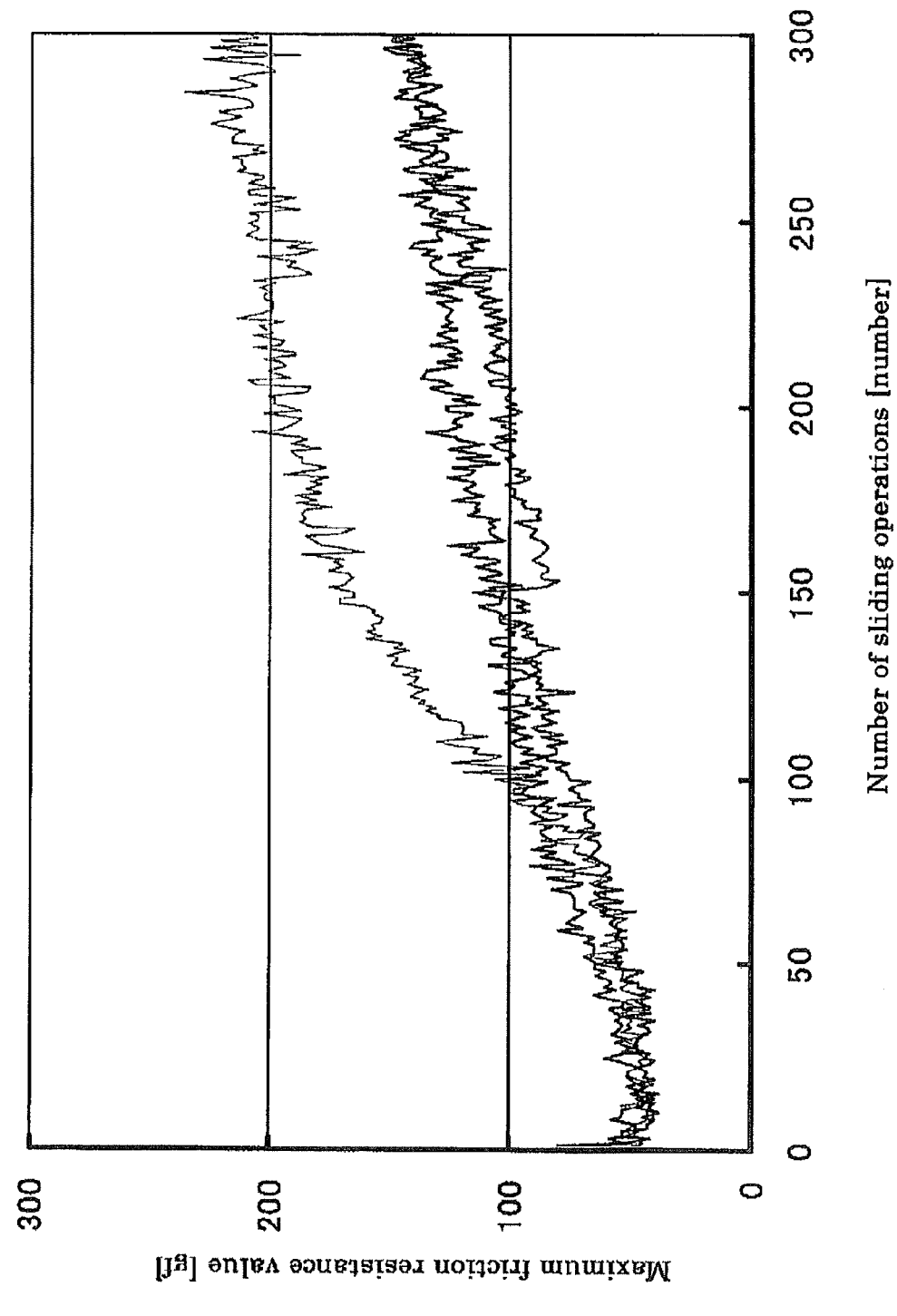
FIG. 7 is a graph showing the results of the evaluation test of the surface lubrication retention of a sheet (sample) of an exemplary medical device having surface lubricity in wet state obtained in Comparative Example 4.

Thereafter, in the same manner as in Example 1, the surface lubrication retention of the sheet (sample) forming the surface lubricating layer 3 according to the above procedure was checked, revealing that although low friction resistance values were initially shown as in FIG. 7, the friction resistance values gradually increased during repetitions of sliding, thus the persistence as a surface lubricating layer being poor.

Example 2

Base Material: LDPE

After ultrasonic cleaning of a low-density polyethylene (LDPE) (Novetec LD LC720, made by Japan Polyethylene Corporation) sheet (30 mm long×50 mm wide×1 mm thick, polymer base layer 1) in acetone, argon ion gas plasma irradiation was carried out for 25 seconds by use of the same plasma irradiation apparatus as used in Example 1 under the same conditions as in Example 1 (plasma treatment prior to coating of a thiol compound).

The LDPE sheet, which had been subjected to the plasma treatment prior to coating of a thiol compound, was immersed in a THF solution of TEMPIC whose concentration was adjusted to 20 mM and naturally dried for 3 minutes. Thereafter, using the plasma irradiation apparatus, argon ion gas plasma irradiation was again carried out for 25 seconds under the same conditions as indicated above (plasma treatment after the coating of the thiol compound). Subsequently, TEMPIC was fixed on the surface of the LDPE sheet by heat treatment in an oven of 80° C. for 12 hours. Moreover, the LDPE sheet, fixed with TEMPIC thereon, was subjected to ultrasonic cleaning in acetone to remove excess TEMPIC, not fixed to the sheet surface. In doing so, the thiol compound 2 covering the entire surface of the base layer 1 (LDPE sheet) and made of TEMPIC was formed (fixed).

After immersion of the TEMPIC-fixed LDPE sheet in a THF solution of a block copolymer dissolved at a rate of 3.5 wt % (block copolymer solution) as used in Example 1, followed by reaction in an oven of 80° C. for 5 hours to form a surface lubricating layer 3 having a thickness (in non-swollen state) of 2 μm and made of the block copolymer (hydrophilic polymer) in such a way as to cover the surface of the thiol compound 2 fixed on the surface of the base layer 1 (LDPE sheet) and made of TEMPIC.

The sheet (sample) wherein the surface lubricating layer 3 had been formed according to the above procedure was fixed inside a petri dish filled with water, which was, in turn, fixed on a trolley table of a friction measuring instrument (Tribomaster TL201Ts, made by Trinity Lab Co., Ltd.). A cylindrical polyethylene terminal (φ20 mm, R 1 mm) was brought into contact on the surface lubricating layer and a load of 200 g was imposed on the terminal. The trolley table set at a rate of 100 cm/minute and a moving distance of 2 cm was horizontally reciprocated 100 times to measure friction resistance values. The maximum friction resistance values in every reciprocation was read out to evaluate surface lubrication retention relative to the 100 cycles of repeated sliding.

Figure 8:
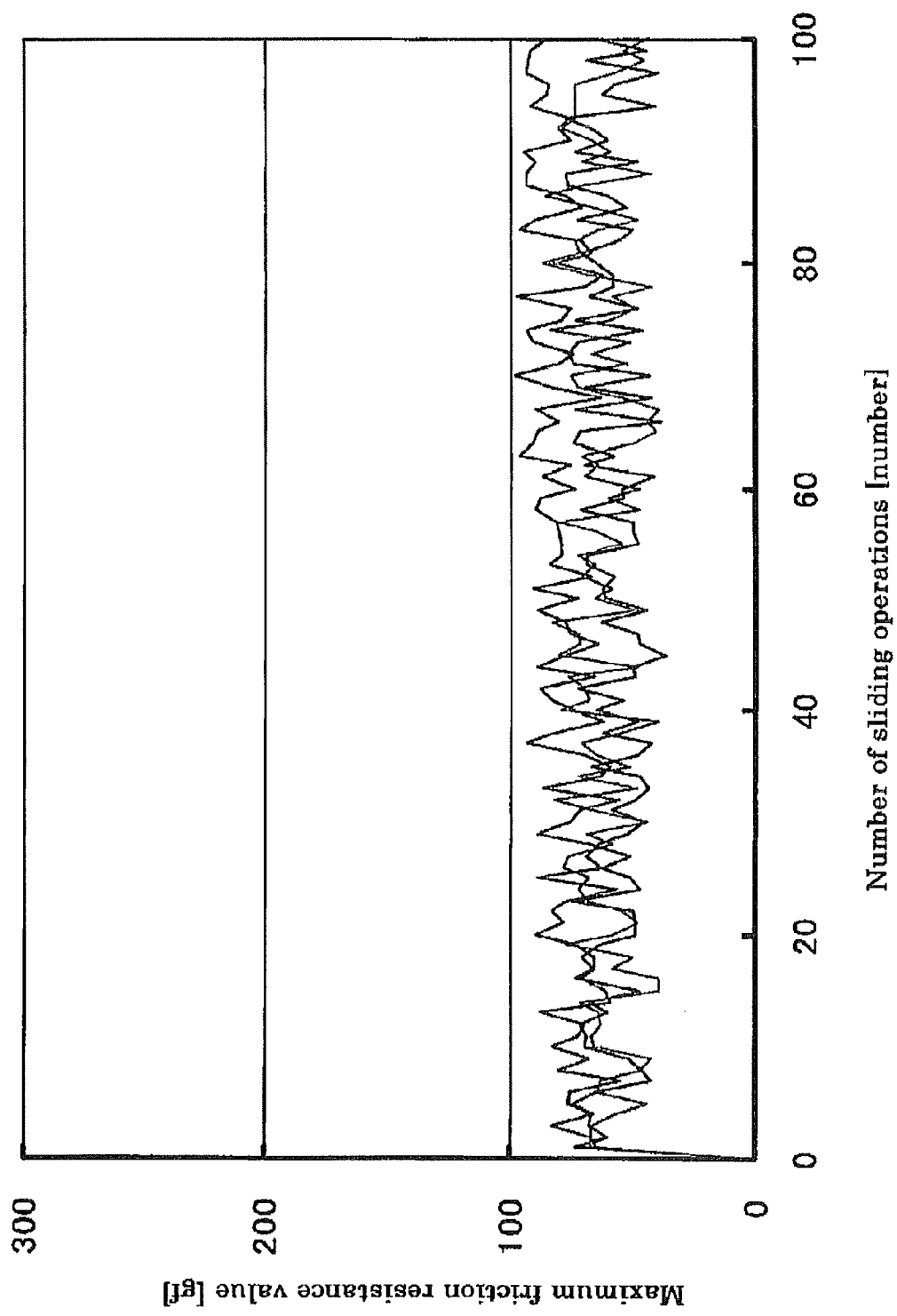
FIG. 8 is a graph showing the results of the evaluation test of the surface lubrication retention of a sheet (sample) of an exemplary medical device having surface lubricity in wet state obtained in Example 2.

As a result of the test, constant maximum friction resistance values are shown as in FIG. 8, demonstrating stable lubricity in 100 cycles of repeated sliding.

Comparative Example 5

Base Material: LDPE

After supersonic cleaning of a LDPE sheet (polymer base layer 1) as used in Example 2 in acetone, the sheet was immersed in the same block copolymer solution as used in Example 2, followed by reaction in an oven of 80° C. for 5 hours to form a surface lubricating layer 3 made of the above block copolymer (hydrophilic polymer) and having a thickness (in non-swollen state) of 2 μm so as to cover the surface of the base layer 1 (LDPE).

Figure 9:
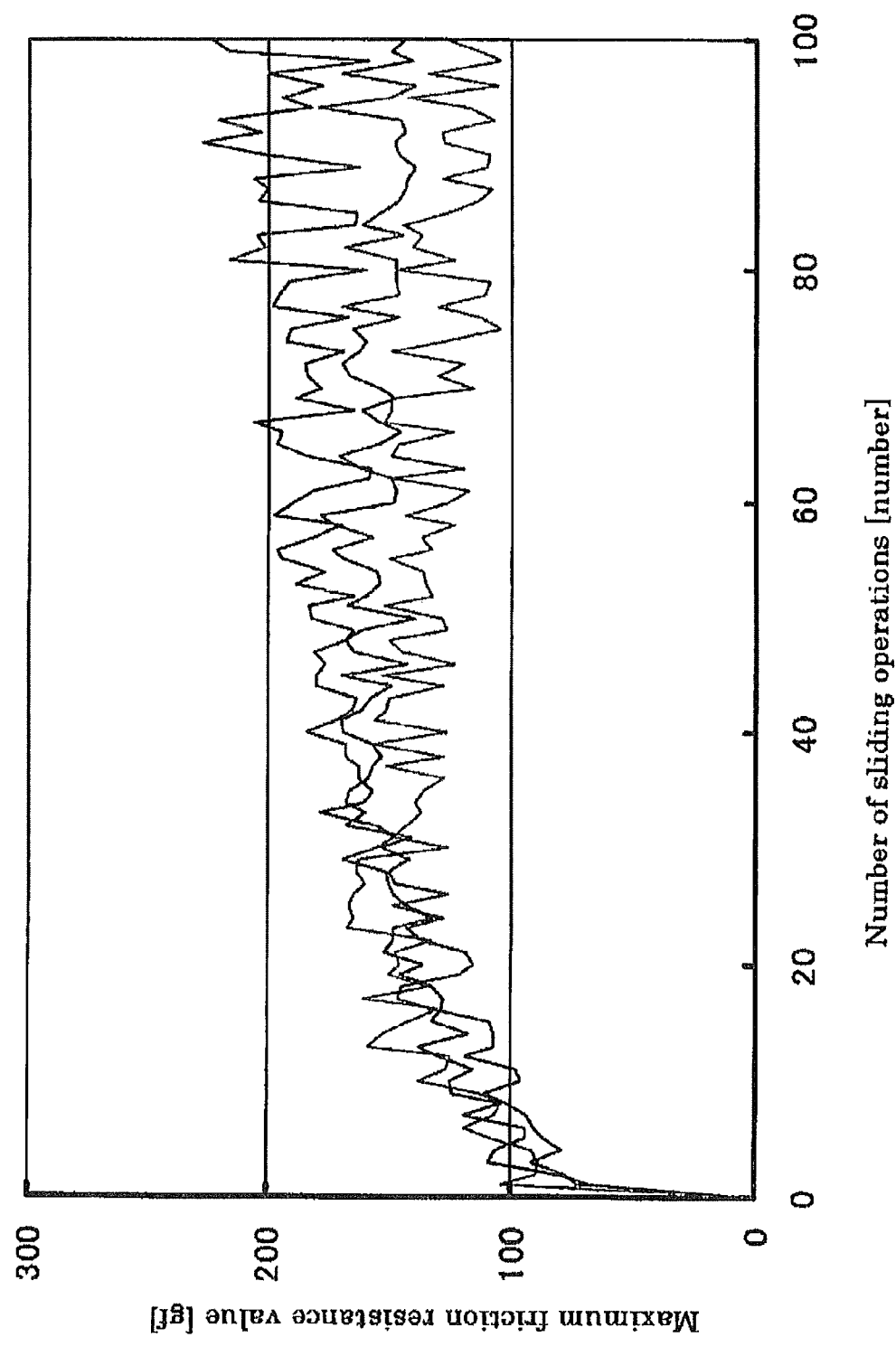
FIG. 9 is a graph showing the results of the evaluation test of the surface lubrication retention of a sheet (sample) of an exemplary medical device having surface lubricity in wet state obtained in Comparative Example 5.

Thereafter, in the same manner as in Example 1, the surface lubricating retention of the sheet (sample) formed with the surface lubricating layer 3 according to the above procedure was checked, revealing that the friction resistance values increased in the course of the repetitions of sliding as shown in FIG. 9, thus the persistence as a surface lubricating layer being poor.

Example 3

Base Material: LDPE

A LDPE sheet (polymer base layer 1) as used in Example 2 was subjected to supersonic cleaning in acetone, immersed in a THF solution of TEMPIC whose concentration was adjusted to 20 mM and naturally dried for 3 minutes. Thereafter, using a plasma irradiation apparatus as in Example 1, argon ion gas plasma treatment was carried out for 25 seconds under the same conditions as in Example 1 (plasma treatment after the coating of the thiol compound). A subsequent heat treatment in an oven of 80° C. for 12 hours permitted TEMPIC to be fixed on the surface of the LDPE sheet. Moreover, the LDPE sheet, on which TEMPIC had been fixed, was subjected to supersonic cleaning in acetone to remove excess TEMPIC, not fixed to the sheet surface. In this way, the thiol compound 2 covering the entire surfaces of the base layer 1 (LDPE sheet) and made of TEMPIC was formed (fixed).

The LDPE sheet, fixed with TEMPIC thereon, was immersed in the same block copolymer solution as used in Example 2, followed by reaction in an oven of 80° C. for 5 hours thereby forming a surface lubricating layer 3 made of the block copolymer (hydrophilic polymer) and having a thickness (in non-swollen state) of 2 μm so as to cover the surface of the thiol compound 2 fixed on the surface of the base layer 1 (LDPE sheet) and made of TEMPIC.

Figure 10:
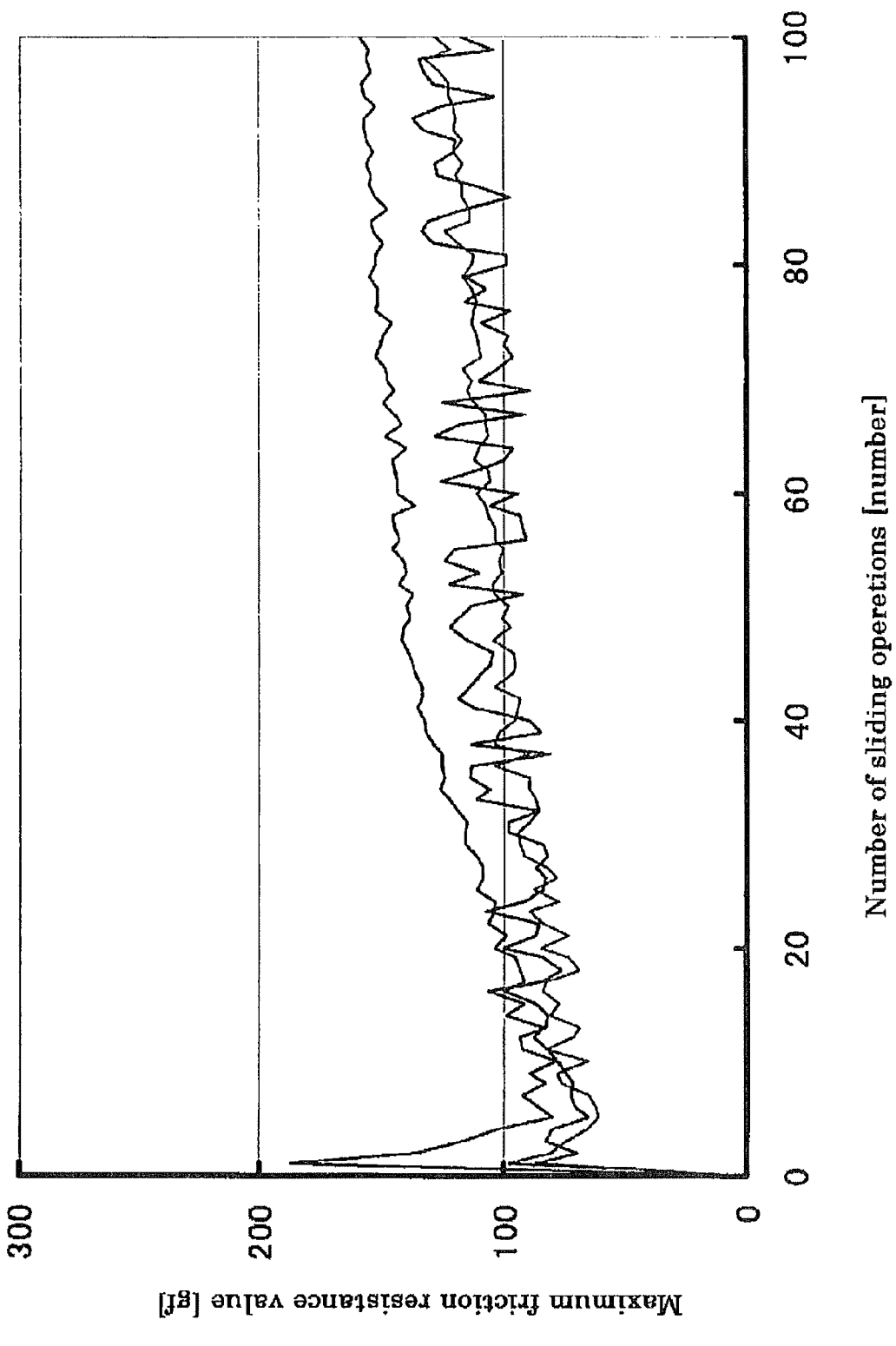
FIG. 10 is a graph showing the results of the evaluation test of the surface lubrication retention of a sheet (sample) of an exemplary medical device having surface lubricity in wet state obtained in Example 3.
Figure 11:
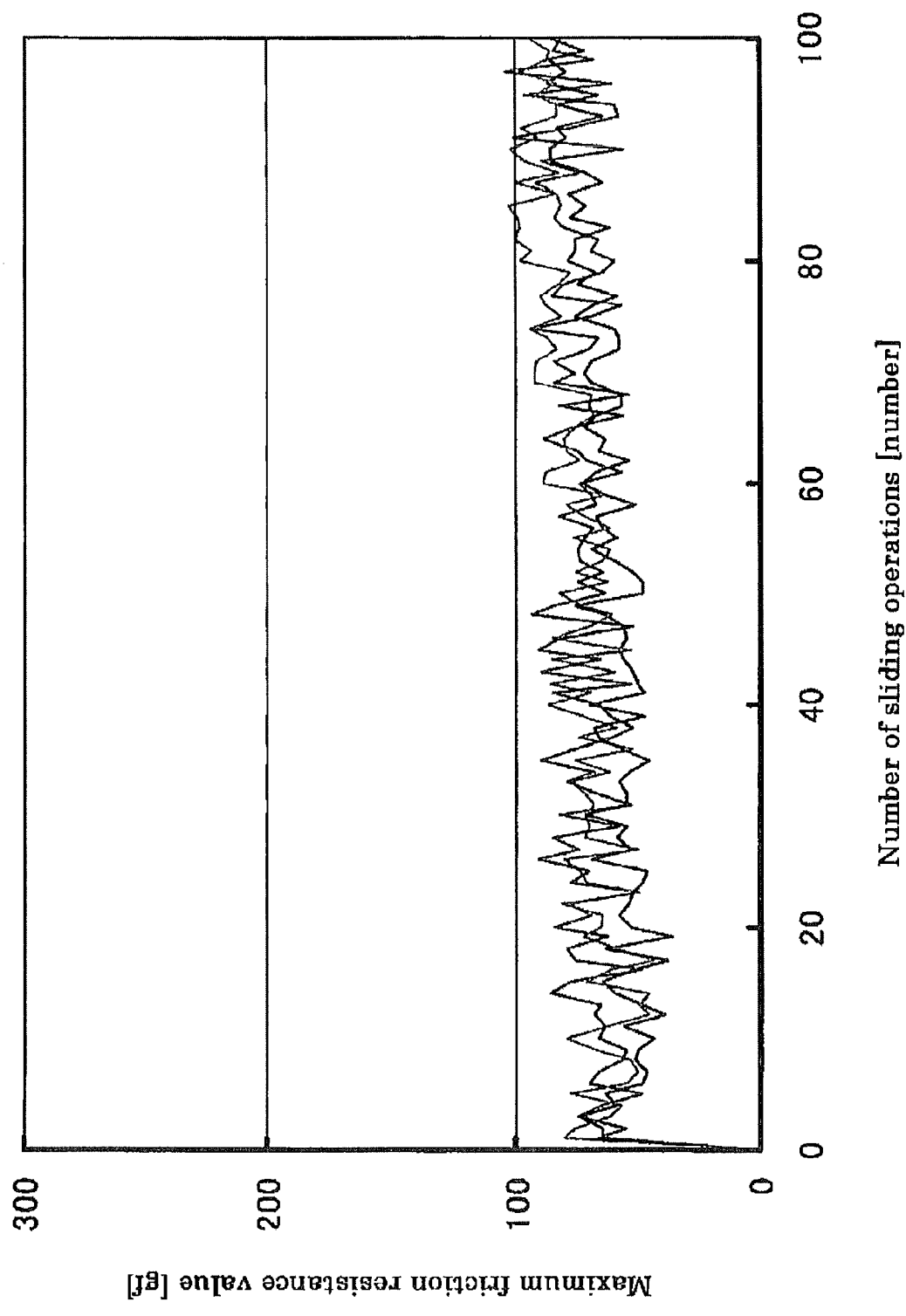
FIG. 11 is a graph showing the results of the evaluation test of the surface lubrication retention of a sheet (sample) of an exemplary medical device having surface lubricity in wet state obtained in Example 4.

Thereafter, in the same manner as in Example 2, the surface lubrication retention of the sheet (sample) on which the surface lubricating layer 3 was formed according to the above procedure was checked, revealing that although the friction resistance values increased in the course of the repetitions of sliding as shown in FIG. 10, the degree of the increase was smaller than with the case of Comparative Example 5 and thus, persistence as a surface lubricating layer was improved.

Example 4

Base Material: LLDPE

In the same manner as in Example 2 except that LDPE of Example 2 was changed to linear low-density polyethylene (LLDPE) (Niporon-Z ZF260, made by Tosoh Corporation), a surface lubricating layer 3 made of the block copolymer (hydrophilic polymer) and having a thickness (in non-swollen state) of 2 μm was formed so as to cover the surface of the thiol compound 2 fixed on the surface of the base layer 1 (LLDPE sheet) and made of TEMPIC. The surface lubrication retention of the resulting sheet (sample) was checked, revealing that the maximum friction resistance values were shown as constant as seen from FIG. 11 and stable lubricity was shown in the course of 100 repetitions of sliding.

Comparative Example 6

Base Material: LLDPE

An LLDPE sheet as used in Example 4 was subjected to ultrasonic cleaning in acetone, and was immersed in such a block copolymer solution as in Example 2, dried and reacted in an oven of 80° C. for 5 hours to form a surface lubricating layer 3 made of the above block copolymer (hydrophilic polymer) and having a thickness (in non-swollen state) of 2 μm so as to cover the surface of the base layer 1 (LLDPE sheet).

Figure 12:
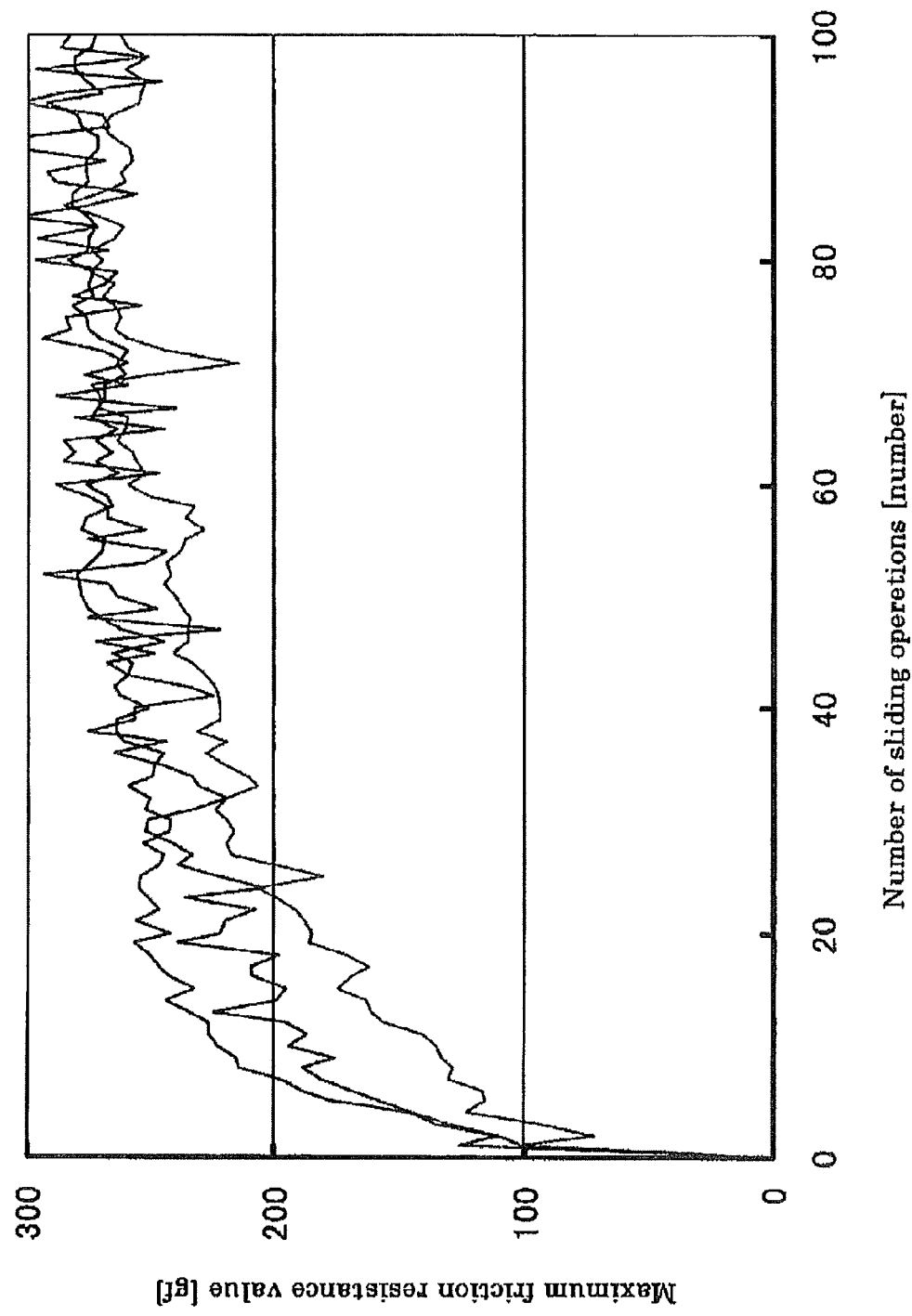
FIG. 12 is a graph showing the results of the evaluation test of the surface lubrication retention of a sheet (sample) of an exemplary medical device having surface lubricity in wet state obtained in Comparative Example 6.

Thereafter, similarly to Example 2, the surface lubrication retention of the sheet (sample), on which the surface lubricating layer 3 had been formed according to the above procedure, was checked, revealing that the friction resistance values gradually increased in the course of repetitions of sliding as shown in FIG. 12 and thus, persistence as a surface lubricating layer was poor.

Example 5

Base Material: HDPE

In the same manner as in Example 2 except that LDPE of Example 2 was changed to high-density polyethylene (HDPE) (Novatec HD HY 540, made by Japan Polyethylene Corporation), a surface lubricating layer 3 made of the block copolymer (hydrophilic polymer) and having a thickness (in non-swollen state) of 2 μm was formed as covering the surface of the thiol compound 2 fixed on the surface of the base layer 1 (HDPE sheet) and made of TEMPIC.

Figure 13:
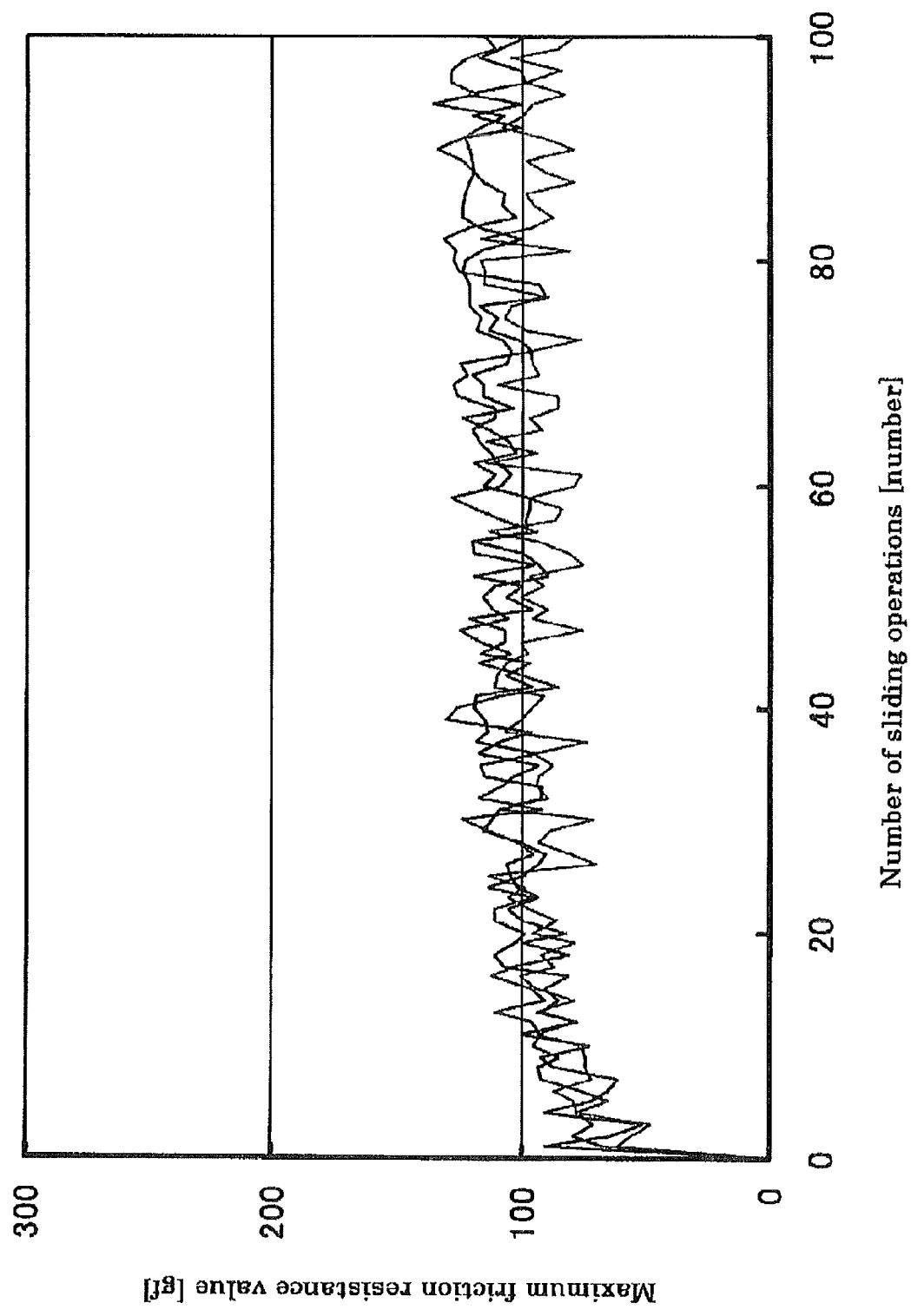
FIG. 13 is a graph showing the results of the evaluation test of the surface lubrication retention of a sheet (sample) of an exemplary medical device having surface lubricity in wet state obtained in Example 5.

Thereafter, the surface lubrication retention of the sheet (sample), on which the surface lubricating layer 3 had been formed according to the above procedure, was checked in the same manner as in Example 2, revealing that although the maximum friction resistance values slightly increased as shown in FIG. 13, the degree of the increase was small and thus, the retention of the surface lubricating layer was high.

Comparative Example 7

Base Layer: HDPE

Such an HDPE sheet as used in Example 5 was subjected to ultrasonic cleaning in acetone, and was immersed in a block copolymer solution as used in Example 2, dried and reacted in an oven of 80° C. for 5 hours to form a surface lubricating layer 3 made of the above block copolymer (hydrophilic polymer) and having a thickness (in non-swollen state) of 2 μm as covering the surface of the base layer 1 (HDPE sheet).

Figure 14:
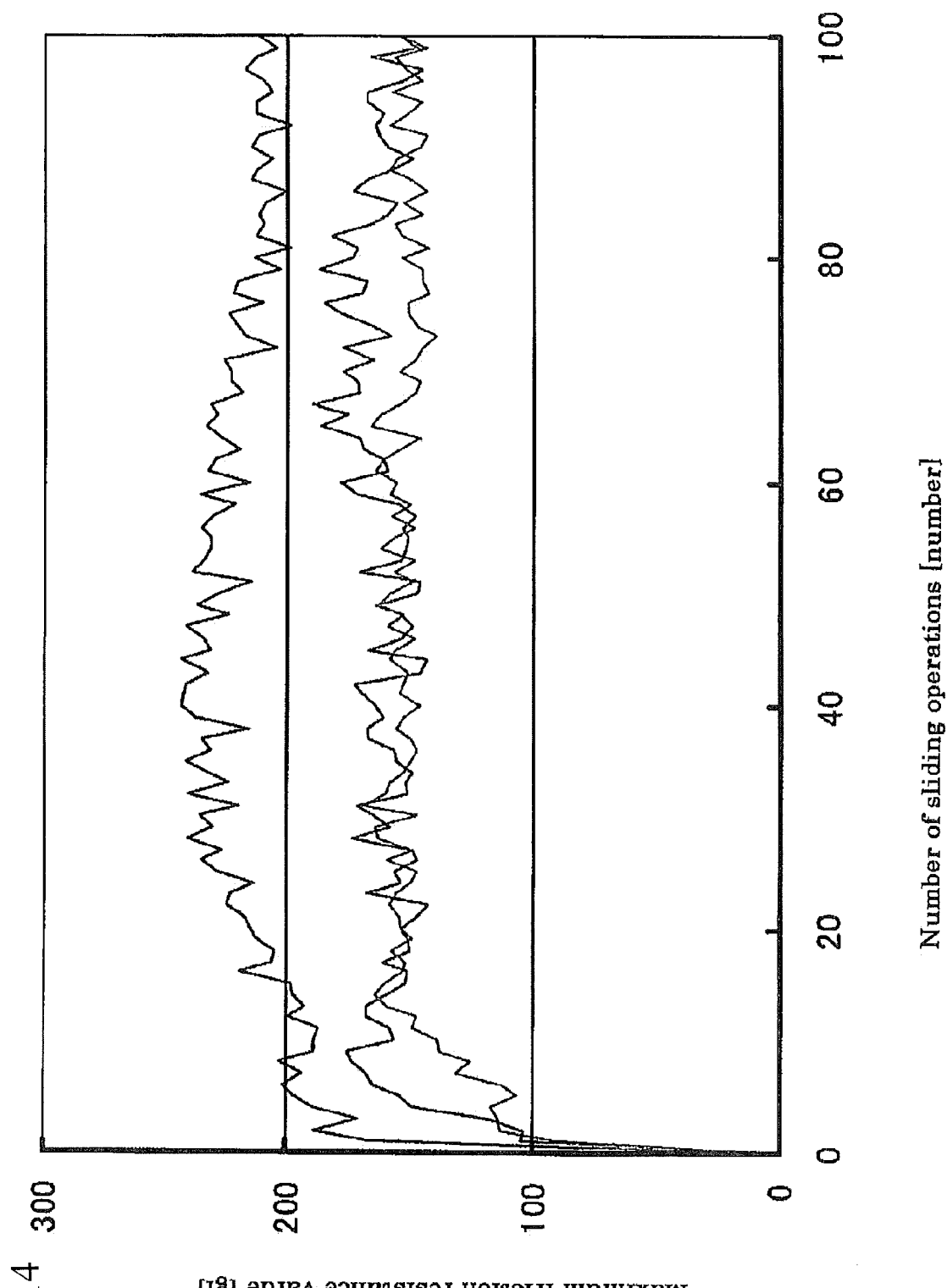
FIG. 14 is a graph showing the results of the evaluation test of the surface lubrication retention of a sheet (sample) of an exemplary medical device having surface lubricity in wet state obtained in Comparative Example 7.

Thereafter, the surface lubrication retention of the sheet (sample), on which the surface lubricating layer 3 had been formed according to the above procedure, was checked in the same manner as in Example 2, revealing that the maximum friction resistance values increased during several repetitions of sliding as shown in FIG. 14 and thus, persistence as a surface lubricating layer was poor.

Reference 1

Base Material: LLDPE

A linear low-density polyethylene (LLDPE) (Niporon-Z ZF260, made by Tosoh Corporation) sheet (10 mm long×10 mm wide×0.3 mm thick, polymer base layer 1) was subjected to supersonic cleaning in acetone. The sheet was subjected to argon ion gas plasma irradiation by use of the same plasma irradiation apparatus as in Example 1 under the same conditions as in Example 1 except that this LLDPE sheet was used in place of the nylon 12 sheet and the argon ion gas plasma irradiation time was changed to 100 seconds (plasma treatment prior to coating of a thiol compound), thereby obtaining the LLDPE sheet subjected to the plasma treatment prior to coating of a thiol compound.

The LLDPE sheet, which had been subjected to the plasma treatment prior to coating of a thiol compound, was immersed in a THF solution of TEMPIC whose concentration was adjusted to 100 mM, naturally dried for 3 minutes and again subjected to argon ion gas plasma irradiation by use of the above plasma irradiation apparatus under the above conditions for 100 seconds (plasma treatment after the coating of the thiol compound). Thereafter, heat treatment was carried out in an oven of 80° C. for 12 hours to fix TEMPIC on the surface of the LLDPE sheet. Moreover, the LLDPE sheet fixed with TEMPIC thereon was subjected to ultrasonic cleaning in THF to remove excess TEMPIC, not fixed on the sheet surface. In this way, the thiol compound 2 made of TEMPIC was formed (fixed) as covering the entire surface of the base layer 1 (LLDPE sheet).

Comparative Reference 1

Base Material: LLDPE

Such a LLDPE sheet (polymer base layer 1) as in Reference 1 was subjected to ultrasonic cleaning in acetone. This LLDPE sheet was immersed in a THF solution of TEMPIC whose concentration was adjusted to 100 mM, naturally dried for 3 minutes and thermally treated in an oven of 80° C. for 12 hours to fix TEMPIC on the surface of the LLDPE sheet. Thereafter, excess TEMPIC, not fixed on the sheet surface, was removed by supersonic cleaning in THF.

Figure 15:
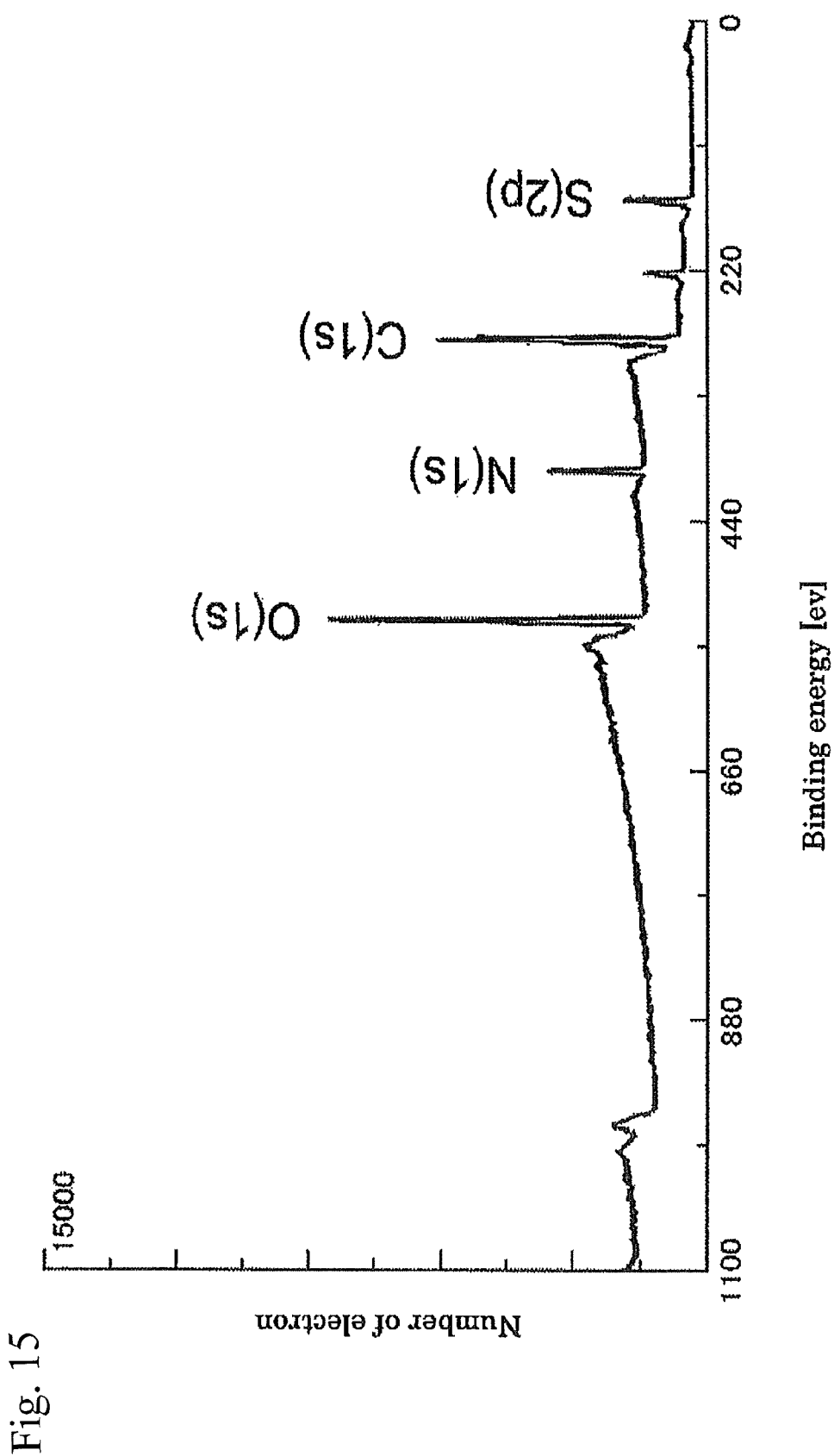
FIG. 15 is a spectrum obtained by analyzing a surface of an exemplary test piece of an LLDPE sheet (plasma-treated) obtained in Reference 1 according to X-ray photoelectron spectroscopy (XPS).
Figure 16:
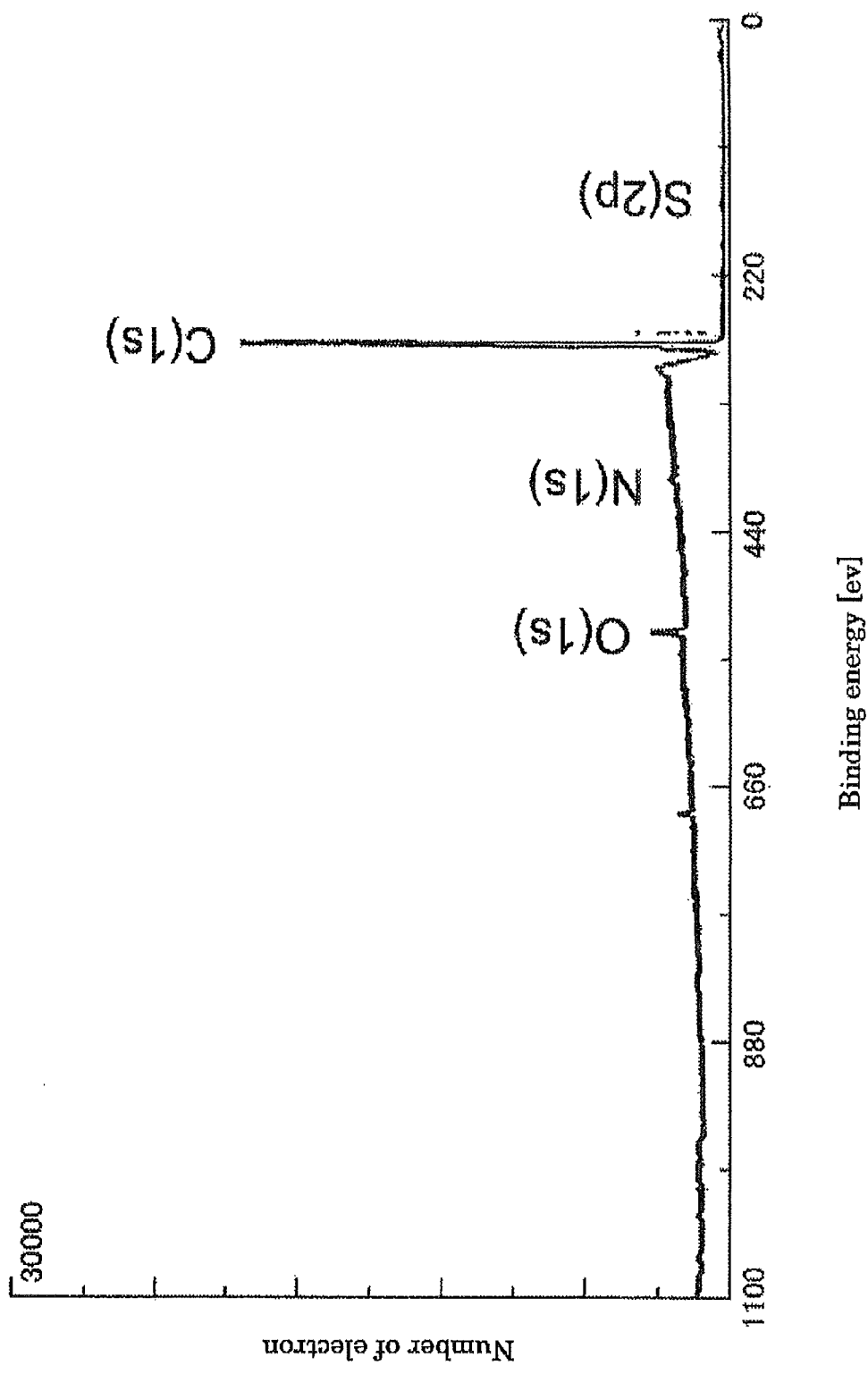
FIG. 16 is a spectrum obtained by analyzing a surface of an exemplary test piece of an LLDPE sheet (not plasma-treated) obtained in Comparative Reference 1 according to X-ray photoelectron spectroscopy (XPS).

The surfaces of the test pieces of the LLDPE sheets obtained in the above Reference 1 (plasma-treated) and Comparative Reference 1 (not plasma-treated) were analyzed according to X-ray photoelectron spectrometry (XPS). The spectrum diagram obtained in Reference 1 is shown in FIG. 15 and the spectrum diagram obtained in Comparative Reference 1 is shown in FIG. 16. In addition, the results of calculation of element ratios of C, N, O and S from the spectra obtained by XPS are shown in Table 1.

TABLE 1

| Elements | Simple substances of TEMPIC | Reference 1 | Comparative Reference 1 |
|---|---|---|---|
| C | 54.5% | 57.3% | 90.6% |
| N | 9.1% | 8.4% | 1.3% |
| O | 27.3% | 28.1% | 4.9% |
| S | 9.1% | 6.2% | 0.5% |

From the results of the above Table 1 and FIGS. 15 and 16, it was confirmed with respect to the XPS spectra that C occupied most of the composition on the surface of Comparative Reference 1 (not plasma-treated), whereas peaks of N, O and S derived from the TEMPIC were clearly observed on the surface of Reference 1. In view of this, with Comparative Example 1, TEMPIC was scarcely fixed on the base layer and was mostly rinsed away by the cleaning operation. In contrast, with Reference 1, it is considered that TEMPIC is strongly fixed on the base layer by the ionized gas plasma irradiation.

Thus, it will be appreciated by those skilled in the art that the present invention can be embodied in other specific forms without departing from the spirit or characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A medical device having surface lubricity in a wet state, comprising:
    a base layer at least a surface of which is made of a polymer material;
    a compound supported on at least a part of said base layer and having three or more thiol groups in one molecule; and
    a surface lubricating layer covering said compound having the thiol groups in the molecule and made of a hydrophilic polymer having a reactive functional group,
    wherein said compound having the thiol groups is supported on the base layer by irradiation of an ionized gas plasma, and said compound having the thiol groups and said hydrophilic polymer having the reactive functional group are reacted to cause the surface lubricating layer to be bound to the base layer,
    wherein the compound having the thiol groups in the molecule comprises 1,3,5-benzenetrithiol, tris-[(3-mercaptopropionyloxy)-ethyl]-isocyanurate, triazinetrithiol, trimethylolpropanetris(3-mercaptopropionate), pentaerythritoltetrakis (mercaptoacetate), pentaerythritoltetrakis(3-mercaptopropionate), pentaerythritoltetrakis(3-mercaptobutylate), dipentaerythritolhexakis(3-mercaptopropionate) or a combination thereof.

2. The medical device having surface lubricity in a wet state according to claim 1, wherein the compound having the thiol groups is supported on the base layer by a process comprising coating a solution dissolving said compound having the thiol groups onto a surface of said base layer, and subsequently irradiating the coating with an ionized gas plasma.

3. The medical device having surface lubricity in a wet state according to claim 2, wherein after coating the solution dissolving said compound having the thiol groups onto the surface of the base layer, and after irradiating the ionized gas plasma, the coating is subjected to a heat treatment.

4. The medical device having surface lubricity in a wet state according to claim 1, wherein the compound having the thiol groups is supported on the base layer by a process comprising irradiating an ionized gas plasma on a surface of said base layer, coating a solution dissolving said compound having the thiol groups onto a surface of said base layer, and irradiating again an ionized gas plasma.

5. The medical device having surface lubricity in a wet state according to claim 4, wherein after coating the solution dissolving said compound having the thiol groups onto the surface of the base layer, and after irradiating the ionized gas plasma, the coating is subjected to a heat treatment.

6. The medical device having surface lubricity in a wet state according to claim 1, wherein the surface of said base layer is irradiated with an ionized gas plasma prior to coating of a solution dissolving said compound having the thiol groups onto the surface of said base layer.

7. The medical device having surface lubricity in a wet state according to claim 6, wherein after coating of the solution dissolving said compound having the thiol groups onto the surface of the base layer, the coating is subjected to a heat treatment.

8. The medical device having surface lubricity in a wet state according to claim 1, wherein the base layer comprises a surface polymer layer and a core portion, wherein the surface polymer layer comprises the polymer material.

9. The medical device having surface lubricity in a wet state according to claim 1, wherein the compound having the thiol groups in the molecule comprises tris-[(3-mercaptopropionyloxy)-ethyl]-isocyanurate, dipentaerythritolhexakis(3-mercaptopropionate) or a combination thereof.

10. The medical device having surface lubricity in a wet state according to claim 1, wherein the surface lubricating layer has a thickness in a non-swollen state of 0.5 to 5 μm.

11. The medical device having surface lubricity in a wet state according to claim 1, wherein the hydrophilic polymer having a reactive functional group comprises an epoxy group or an isocyanate group.

12. The medical device having surface lubricity in a wet state according to claim 1, wherein the hydrophilic polymer of the surface lubricating layer covers the entire surface of the compound having the thiol groups.

13. The medical device having surface lubricity in a wet state according to claim 12, wherein the compound having the thiol groups is uniformly coated on the base layer.

14. The medical device having surface lubricity in a wet state according to claim 12, wherein the compound having the thiol groups forms a monomolecular layer.

15. A method of making the medical device having surface lubricity in a wet state according to claim 1, the method comprising irradiating the surface of the base layer or a coating formed from the compound having a plurality of thiol groups, with an ionized gas plasma.

* * * * *